(12) United States Patent
Faulhaber

(10) Patent No.: US 11,759,331 B2
(45) Date of Patent: Sep. 19, 2023

(54) STABILIZED EXPANDABLE INTERVERTEBRAL SPACER

(71) Applicant: GLOBUS MEDICAL, INC., Audubon, PA (US)

(72) Inventor: Kurt Faulhaber, Renton, WA (US)

(73) Assignee: Globus Medical, Inc., Audubon, PA (US)

( * ) Notice: Subject to any disclaimer, the term of this patent is extended or adjusted under 35 U.S.C. 154(b) by 268 days.

(21) Appl. No.: 17/346,456

(22) Filed: Jun. 14, 2021

(65) Prior Publication Data

US 2021/0298915 A1 Sep. 30, 2021

Related U.S. Application Data

(60) Continuation of application No. 16/255,994, filed on Jan. 24, 2019, now Pat. No. 11,033,404, which is a division of application No. 14/937,198, filed on Nov. 10, 2015, now Pat. No. 10,219,914.

(51) Int. Cl.
*A61F 2/44* (2006.01)
*A61F 2/30* (2006.01)

(52) U.S. Cl.
CPC .......... *A61F 2/447* (2013.01); *A61F 2/30767* (2013.01); *A61F 2002/30507* (2013.01); *A61F 2002/30556* (2013.01); *A61F 2002/30579* (2013.01); *A61F 2002/30593* (2013.01); *A61F 2002/30622* (2013.01); *A61F 2002/30843* (2013.01); *A61F 2002/30904* (2013.01)

(58) Field of Classification Search
None
See application file for complete search history.

(56) References Cited

U.S. PATENT DOCUMENTS

| 4,349,921 A | 9/1982 | Kuntz |
|---|---|---|
| 4,599,086 A | 7/1986 | Doty |
| 4,863,476 A | 9/1989 | Shepperd |
| 4,863,477 A | 9/1989 | Monson |
| 5,123,926 A | 6/1992 | Pisharodi |
| 5,290,312 A | 3/1994 | Kojimoto et al. |
| 5,306,310 A | 4/1994 | Siebels |
| 5,375,823 A | 12/1994 | Navas |

(Continued)

FOREIGN PATENT DOCUMENTS

| CA | 2088066 A1 | 1/1992 |
|---|---|---|
| DE | 4012622 C1 | 7/1991 |

(Continued)

*Primary Examiner* — Sameh R Boles

(57) ABSTRACT

A spacer for separating bones of a joint, the spacer includes a first endplate configured to engage a first bone of the joint, and comprising a ramped surface; a tissue engaging subassembly disposed in a compartment of the first endplate; a second endplate configured to engage a second bone of the joint; and a frame subassembly that extends between the first endplate and the second endplate. The frame subassembly comprises a drive nut, a drive shaft coupled to the drive nut, a ramped carriage coupled to the drive shaft, wherein the ramped carriage comprises a ramped surface operable to engage the ramped surface of the first endplate, and an actuation bar coupled to the drive nut comprising a plate operable to engage the tissue engaging subassembly.

20 Claims, 18 Drawing Sheets

(56) References Cited

U.S. PATENT DOCUMENTS

| | | |
|---|---|---|
| 5,390,683 A | 2/1995 | Pisharodi |
| 5,522,899 A | 6/1996 | Michelson |
| 5,534,030 A | 7/1996 | Navarro et al. |
| 5,554,191 A | 9/1996 | Lahille et al. |
| 5,571,192 A | 11/1996 | Schonhoffer |
| 5,645,596 A | 7/1997 | Kim |
| 5,653,763 A | 8/1997 | Errico et al. |
| 5,655,122 A | 8/1997 | Wu |
| 5,665,122 A | 9/1997 | Kambin |
| 5,676,701 A | 10/1997 | Yuan et al. |
| 6,039,761 A | 3/2000 | Li et al. |
| 6,045,579 A | 4/2000 | Hochschuler et al. |
| 6,080,193 A | 6/2000 | Hochschuler et al. |
| 6,099,531 A | 8/2000 | Bonutti |
| 6,126,689 A | 10/2000 | Brett |
| 6,176,882 B1 | 1/2001 | Biedermann et al. |
| 6,258,125 B1 | 7/2001 | Paul et al. |
| 6,419,705 B1 | 7/2002 | Erickson |
| 6,558,423 B1 | 5/2003 | Michelson |
| 6,562,074 B2 | 5/2003 | Gerbec et al. |
| 6,576,016 B1 | 6/2003 | Hochschuler et al. |
| 6,554,863 B2 | 8/2003 | Paul et al. |
| 6,641,614 B1 | 11/2003 | Wagner et al. |
| 6,648,917 B2 | 11/2003 | Gerbec et al. |
| 6,666,891 B2 | 12/2003 | Boehm, Jr. et al. |
| 6,692,495 B1 | 2/2004 | Zacouto |
| 6,706,070 B1 | 3/2004 | Wagner et al. |
| 6,752,832 B2 | 6/2004 | Ulrich |
| 6,814,756 B1 | 11/2004 | Michelson |
| 6,830,589 B2 | 12/2004 | Erickson |
| 6,849,093 B2 | 2/2005 | Michelson |
| 6,852,129 B2 | 2/2005 | Gerbec et al. |
| 6,863,673 B2 | 3/2005 | Gerbec et al. |
| 6,881,228 B2 | 4/2005 | Zdeblick et al. |
| 7,018,415 B1 | 3/2006 | McKay |
| 7,070,598 B2 | 7/2006 | Lim et al. |
| 7,204,853 B2 | 4/2007 | Gordon |
| 7,217,291 B2 | 5/2007 | Zucherman et al. |
| 7,282,063 B2 | 10/2007 | Cohen et al. |
| 7,316,714 B2 | 1/2008 | Gordon |
| 7,473,276 B2 | 1/2009 | Aebi et al. |
| 7,547,325 B2 | 6/2009 | Biedermann et al. |
| 7,621,953 B2 | 11/2009 | Braddock, Jr. et al. |
| 7,641,693 B2 | 1/2010 | Gutlin et al. |
| 7,682,396 B2 | 3/2010 | Beaurain et al. |
| 7,749,270 B2 | 7/2010 | Peterman |
| 7,753,958 B2 | 7/2010 | Gordon |
| 7,771,473 B2 | 8/2010 | Thramann |
| 7,780,732 B2 | 8/2010 | Abernathie |
| 7,799,058 B2 | 9/2010 | Froehlich |
| 7,799,081 B2 | 9/2010 | McKinley |
| 7,815,683 B2 | 10/2010 | Melkent et al. |
| 7,837,734 B2 | 11/2010 | Zucherman et al. |
| 7,875,078 B2 | 1/2011 | Wysocki et al. |
| 7,901,409 B2 | 3/2011 | Canaveral et al. |
| 7,909,869 B2 | 3/2011 | Gordon |
| 7,951,199 B2 | 5/2011 | Miller |
| 7,985,256 B2 | 7/2011 | Grotz et al. |
| 8,062,375 B2 | 11/2011 | Glerum et al. |
| 8,070,813 B2 | 12/2011 | Grotz et al. |
| 8,123,810 B2 | 2/2012 | Gordon |
| 8,137,405 B2 | 3/2012 | Kostuik et al. |
| 8,192,495 B2 | 6/2012 | Simpson et al. |
| 8,303,663 B2 | 11/2012 | Jimenez et al. |
| 8,377,140 B2 | 2/2013 | DeFalco et al. |
| 8,394,143 B2 | 3/2013 | Grotz et al. |
| 8,435,296 B2 | 5/2013 | Kadaba et al. |
| 8,454,695 B2 | 6/2013 | Grotz et al. |
| 8,647,386 B2 | 2/2014 | Gordon |
| 8,696,751 B2 | 4/2014 | Ashley et al. |
| 8,771,360 B2 | 7/2014 | Jimenez et al. |
| 8,894,710 B2 | 11/2014 | Simpson et al. |
| 8,932,355 B2 | 1/2015 | Grotz et al. |
| 8,940,049 B1 | 1/2015 | JImenez et al. |
| 8,956,413 B2 | 2/2015 | Ashley et al. |
| 8,992,620 B2 | 3/2015 | Ashley et al. |
| 9,028,550 B2 | 5/2015 | Shulock et al. |
| 9,358,125 B2 | 6/2016 | Jimenez et al. |
| 9,532,883 B2 | 1/2017 | McLuen et al. |
| 9,622,878 B2 | 4/2017 | Grotz |
| 2002/0045945 A1 | 4/2002 | Liu |
| 2002/0068976 A1 | 6/2002 | Jackson |
| 2002/0068977 A1 | 6/2002 | Jackson |
| 2004/0030387 A1 | 2/2004 | Landry |
| 2004/0049271 A1 | 3/2004 | Biedermann |
| 2004/0054412 A1 | 3/2004 | Gerbec et al. |
| 2004/0087947 A1 | 5/2004 | Lim et al. |
| 2004/0153065 A1 | 8/2004 | Lim |
| 2005/0021041 A1 | 1/2005 | Michelson |
| 2005/0021145 A1 | 1/2005 | de Villiers et al. |
| 2005/0033432 A1 | 2/2005 | Gordon |
| 2005/0080422 A1 | 4/2005 | Otte |
| 2005/0113916 A1 | 5/2005 | Branch, Jr. |
| 2005/0149188 A1 | 7/2005 | Cook |
| 2005/0171541 A1 | 8/2005 | Boehm |
| 2005/0222681 A1 | 10/2005 | Richley |
| 2005/0251258 A1 | 11/2005 | Jackson |
| 2005/0273171 A1 | 12/2005 | Gordon |
| 2005/0273174 A1 | 12/2005 | Gordon |
| 2005/0278026 A1 | 12/2005 | Gordon |
| 2005/0283244 A1 | 12/2005 | Gordon |
| 2005/0283245 A1 | 12/2005 | Gordon |
| 2006/0004453 A1 | 1/2006 | Bartish et al. |
| 2006/0015184 A1 | 1/2006 | Winterbottom |
| 2006/0058878 A1 | 3/2006 | Michelson |
| 2006/0084986 A1 | 4/2006 | Grinberg |
| 2006/0122701 A1 | 6/2006 | Kister |
| 2006/0129244 A1 | 6/2006 | Ensign |
| 2006/0142859 A1 | 6/2006 | Mcluen |
| 2006/0149385 A1 | 7/2006 | Mckay |
| 2006/0195192 A1 | 8/2006 | Gordon et al. |
| 2006/0229729 A1 | 10/2006 | Gordon |
| 2006/0241770 A1 | 10/2006 | Rhoda |
| 2006/0253201 A1 | 11/2006 | Mcluen |
| 2007/0043442 A1 | 2/2007 | Abernathie |
| 2007/0050030 A1 | 3/2007 | Kim |
| 2007/0050032 A1 | 3/2007 | Gittings et al. |
| 2007/0055377 A1 | 3/2007 | Hanson et al. |
| 2007/0191951 A1 | 8/2007 | Branch |
| 2007/0255415 A1 | 11/2007 | Edie et al. |
| 2007/0270963 A1 | 11/2007 | Melkent et al. |
| 2007/0270968 A1 | 11/2007 | Baynham |
| 2008/0021559 A1 | 1/2008 | Thramann |
| 2008/0065222 A1 | 3/2008 | Hamada |
| 2008/0114467 A1 | 5/2008 | Capote |
| 2008/0140207 A1 | 6/2008 | Olmos et al. |
| 2008/0147194 A1 | 6/2008 | Grotz |
| 2008/0161933 A1 | 7/2008 | Grotz et al. |
| 2008/0167657 A1 | 7/2008 | Greenhalgh |
| 2008/0183204 A1 | 7/2008 | Greenhalgh et al. |
| 2008/0221694 A1 | 9/2008 | Warnick |
| 2008/0275455 A1 | 11/2008 | Berry et al. |
| 2008/0281346 A1 | 11/2008 | Greenhalgh et al. |
| 2008/0288073 A1 | 11/2008 | Renganath et al. |
| 2008/0300598 A1 | 12/2008 | Barreiro et al. |
| 2008/0306488 A1 | 12/2008 | Altarac et al. |
| 2008/0319487 A1 | 12/2008 | Fielding et al. |
| 2008/0319549 A1 | 12/2008 | Greenhalgh et al. |
| 2009/0024217 A1 | 1/2009 | Levy et al. |
| 2009/0076616 A1 | 3/2009 | Duggal |
| 2009/0125062 A1 | 5/2009 | Amin |
| 2009/0149956 A1 | 6/2009 | Greenhalgh et al. |
| 2009/0149959 A1 | 6/2009 | Conner et al. |
| 2009/0204218 A1 | 8/2009 | Richelsoph |
| 2009/0222100 A1 | 9/2009 | Cipoletti et al. |
| 2009/0240334 A1 | 9/2009 | Richelsoph |
| 2009/0270989 A1 | 10/2009 | Conner et al. |
| 2009/0281628 A1 | 11/2009 | Oglaza et al. |
| 2009/0292361 A1 | 11/2009 | Lopez |
| 2009/0299478 A1 | 12/2009 | Carls et al. |
| 2009/0312763 A1 | 12/2009 | McCormack |
| 2010/0049324 A1 | 2/2010 | Valdevit |
| 2010/0070041 A1 | 3/2010 | Peterman |
| 2010/0082109 A1 | 4/2010 | Greenhalgh et al. |

(56) References Cited

U.S. PATENT DOCUMENTS

| | | |
|---|---|---|
| 2010/0145455 A1 | 6/2010 | Simpson et al. |
| 2010/0179657 A1 | 7/2010 | Greenhalgh et al. |
| 2010/0185291 A1 | 7/2010 | Jimenez |
| 2010/0191336 A1 | 7/2010 | Greenhalgh |
| 2010/0204795 A1 | 8/2010 | Greenhalgh |
| 2010/0211176 A1 | 8/2010 | Greenhalgh |
| 2010/0222816 A1 | 9/2010 | Gabelberger et al. |
| 2010/0222884 A1 | 9/2010 | Greenhalgh |
| 2010/0234952 A1 | 9/2010 | Peterman |
| 2010/0249933 A1 | 9/2010 | Tried |
| 2010/0280622 A1 | 11/2010 | Mckinley |
| 2010/0286779 A1 | 11/2010 | Thibodeau |
| 2010/0286780 A1 | 11/2010 | Dryer |
| 2010/0286783 A1 | 11/2010 | Lechmann |
| 2010/0292796 A1 | 11/2010 | Greenhalgh |
| 2010/0305705 A1 | 12/2010 | Butler |
| 2010/0331981 A1 | 12/2010 | Mohammed |
| 2010/0331985 A1 | 12/2010 | Gordon |
| 2011/0035011 A1 | 2/2011 | Cain |
| 2011/0093074 A1 | 4/2011 | Glerum |
| 2011/0160861 A1 | 6/2011 | Jimenez |
| 2011/0172774 A1 | 7/2011 | Varela |
| 2011/0184522 A1 | 7/2011 | Melkent et al. |
| 2011/0276142 A1 | 11/2011 | Niemiec |
| 2011/0301713 A1 | 12/2011 | Theofilos |
| 2011/0319997 A1 | 12/2011 | Glerum |
| 2012/0035729 A1 | 2/2012 | Glerum |
| 2012/0059470 A1 | 3/2012 | Weiman |
| 2012/0059472 A1 | 3/2012 | Weiman |
| 2012/0109308 A1 | 5/2012 | Lechmann |
| 2012/0130496 A1 | 5/2012 | Duffield |
| 2012/0165945 A1 | 6/2012 | Hansell |
| 2012/0185049 A1 | 7/2012 | Varela |
| 2012/0209386 A1 | 8/2012 | Triplett |
| 2012/0215313 A1 | 8/2012 | Saidha |
| 2012/0265309 A1 | 10/2012 | Glerum |
| 2012/0277861 A1 | 11/2012 | Steele et al. |
| 2012/0277870 A1 | 11/2012 | Wolters |
| 2012/0323329 A1 | 12/2012 | Jimenez |
| 2012/0330426 A1 | 12/2012 | McLaughlin |
| 2013/0023993 A1 | 1/2013 | Weiman |
| 2013/0023994 A1* | 1/2013 | Glerum |
| 2013/0158669 A1 | 6/2013 | Sungarian |
| 2013/0274883 A1 | 10/2013 | McLuen et al. |
| 2014/0088714 A1 | 3/2014 | Miller et al. |
| 2015/0066145 A1 | 3/2015 | Rogers et al. |
| 2015/0088258 A1 | 3/2015 | Jimenez et al. |
| 2015/0134064 A1 | 5/2015 | Grotz et al. |
| 2015/0216676 A1 | 8/2015 | Shulock et al. |
| 2015/0289988 A1 | 10/2015 | Ashley et al. |
| 2015/0374508 A1 | 12/2015 | Sandul |
| 2016/0166396 A1 | 6/2016 | McClintock |
| 2016/0324654 A1 | 11/2016 | Loebl et al. |
| 2016/0338850 A1* | 11/2016 | Ashleigh ............... A61F 2/4611 |
| 2017/0100258 A1 | 4/2017 | Jimenez et al. |
| 2017/0119543 A1 | 5/2017 | Dietzel et al. |

FOREIGN PATENT DOCUMENTS

| | | |
|---|---|---|
| DE | 4327054 C1 | 4/1995 |
| EP | 0576379 B1 | 6/1993 |
| EP | 0610837 B1 | 7/1994 |
| EP | 3111896 A1 | 1/2017 |
| FR | 2794968 A1 | 12/2000 |
| JP | 2000-513263 A | 10/2000 |
| SU | 1424826 A1 | 9/1988 |
| WO | 9201428 A1 | 2/1992 |
| WO | 9525485 A1 | 9/1995 |
| WO | 199942062 A1 | 8/1999 |
| WO | 199966867 A1 | 12/1999 |
| WO | 2002045625 A1 | 6/2002 |
| WO | 2004019829 A1 | 3/2004 |
| WO | 2004069033 A2 | 8/2004 |
| WO | 2006045094 A2 | 10/2005 |
| WO | 2006045094 A2 | 4/2006 |
| WO | 2006047587 A2 | 5/2006 |
| WO | 2006113080 A2 | 10/2006 |
| WO | 2008044057 A1 | 10/2007 |
| WO | 2008044057 A1 | 4/2008 |
| WO | 2008134515 A1 | 11/2008 |
| WO | 2009114381 A1 | 9/2009 |
| WO | 2012031267 A1 | 3/2012 |

* cited by examiner

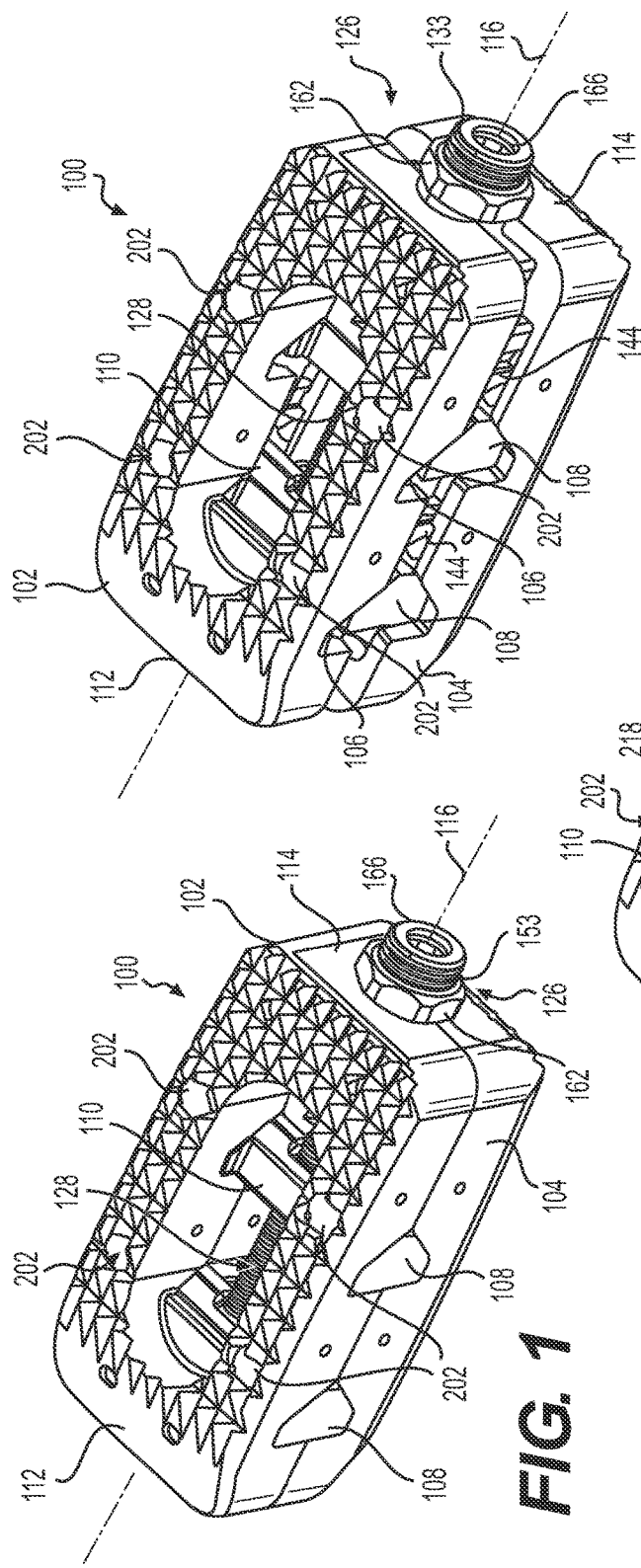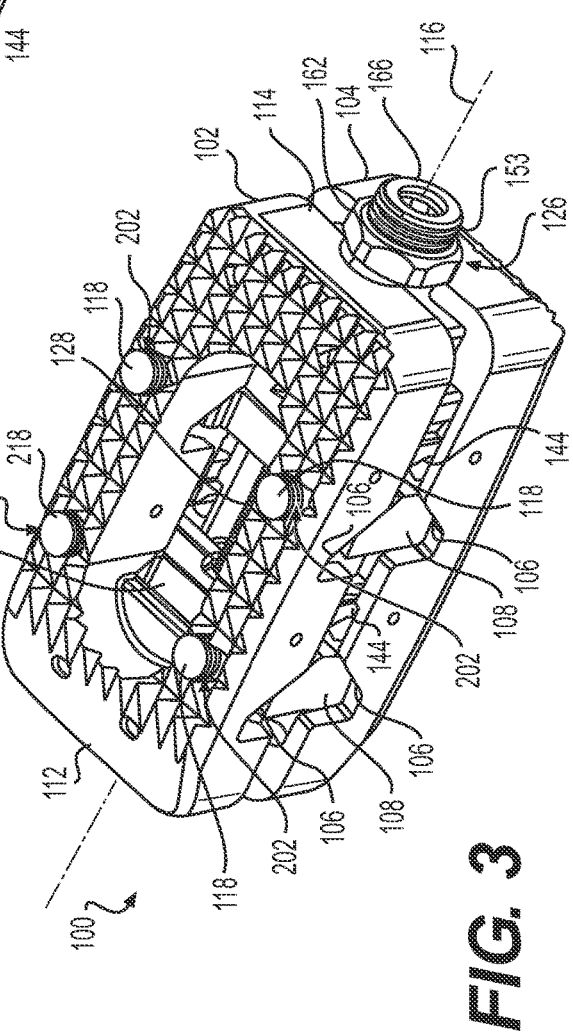

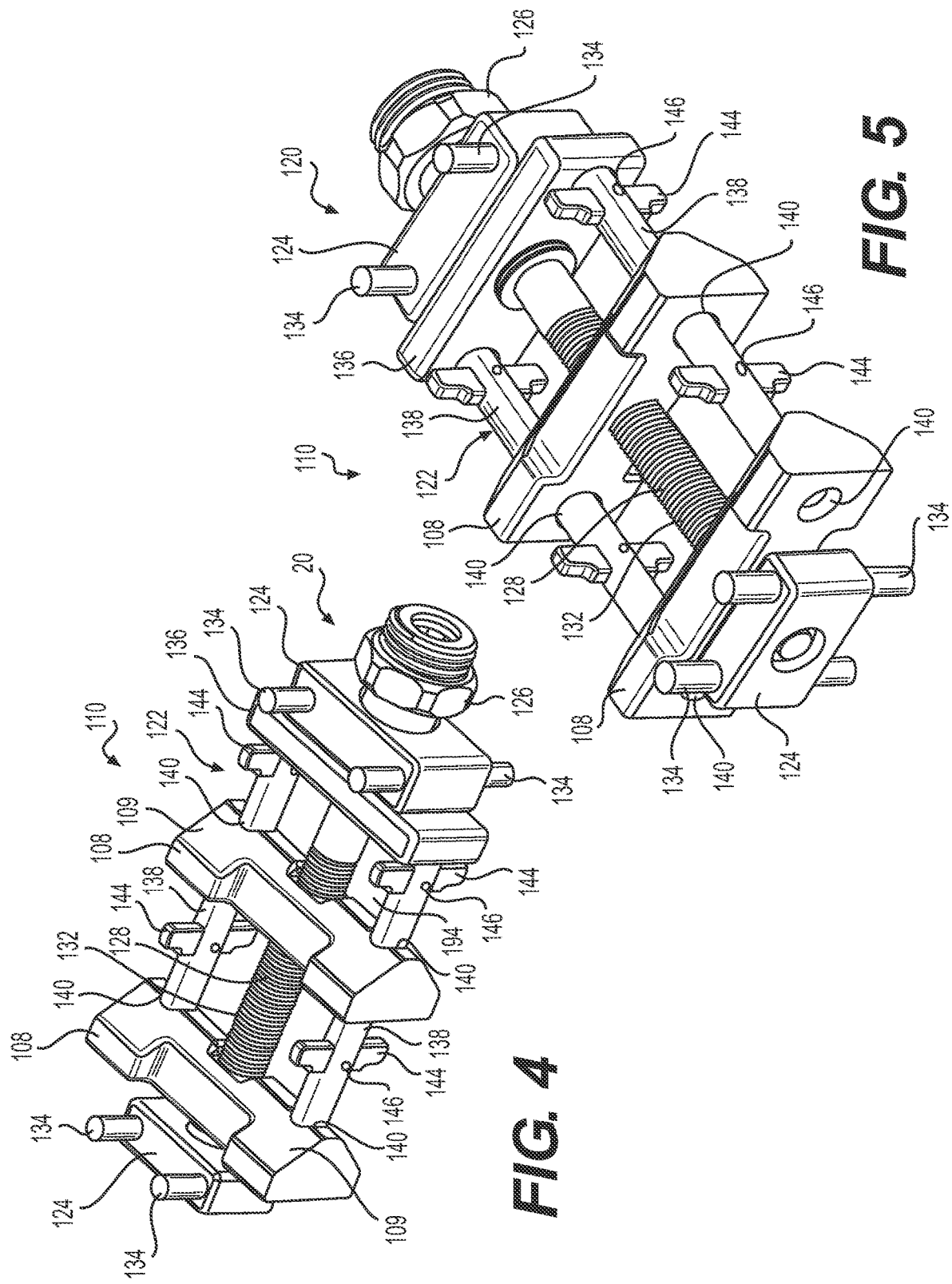

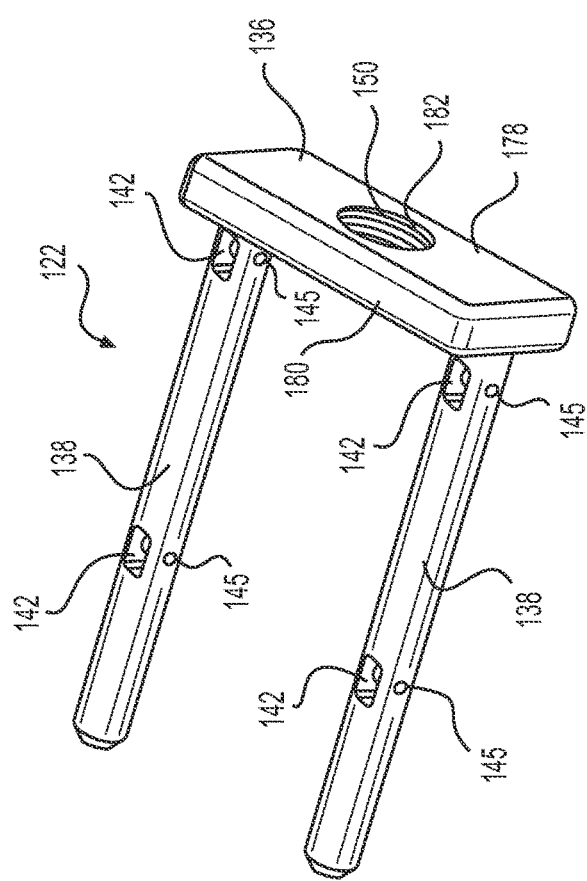
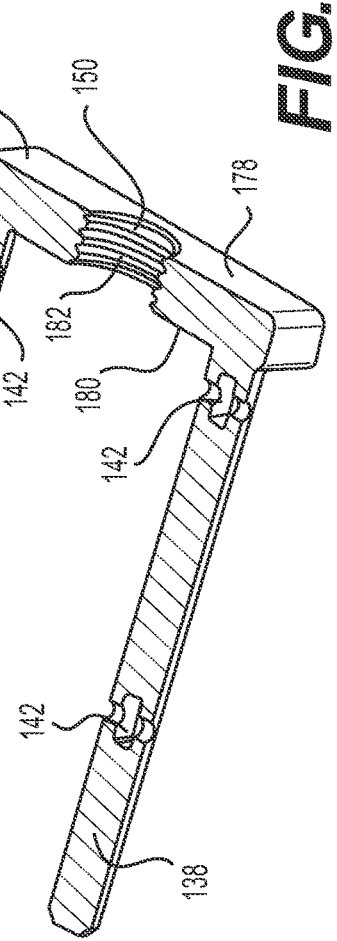

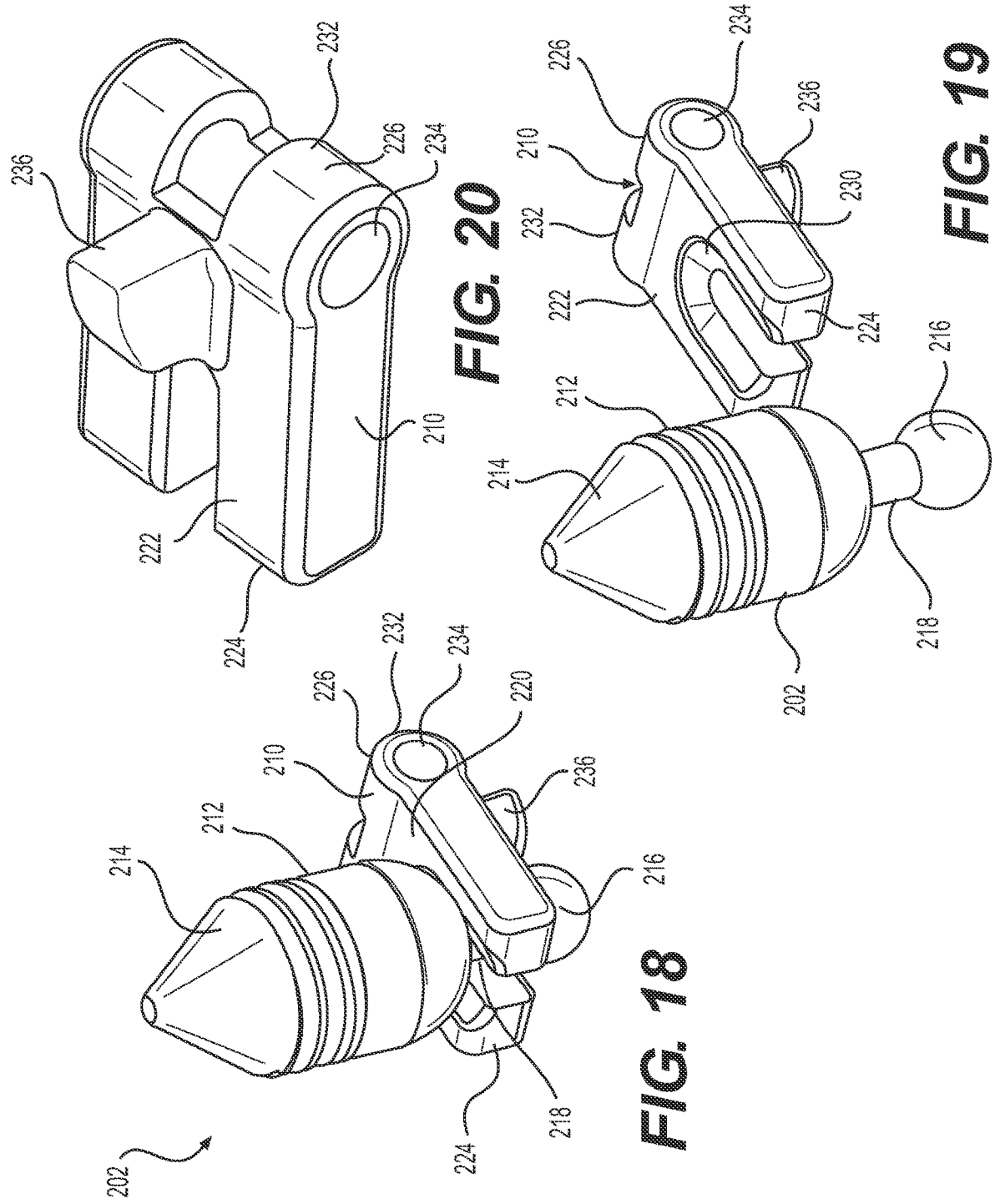

STABILIZED EXPANDABLE INTERVERTEBRAL SPACER

CROSS REFERENCE TO RELATED APPLICATION

This application is continuation of U.S. patent application Ser. No. 16/255,994, filed Jan. 24, 2019, which is a divisional of U.S. patent application Ser. No. 14/937,198, filed Nov. 10, 2015, all of which are incorporated by reference herein in their entirety for all purposes.

FIELD OF THE INVENTION

This invention relates to stabilizing adjacent vertebrae of the spine by inserting an intervertebral spacer, and more particularly an intervertebral spacer that is stabilized and adjustable in height.

BACKGROUND

The vertebral or spinal column (spine, backbone) is a flexible assembly of vertebrae stacked on top of each other extending from the skull to the pelvic bone which acts to support the axial skeleton and to protect the spinal cord and nerves. The vertebrae are anatomically organized into four generalized body regions identified as cervical, thoracic, lumbar, and sacral; the cervical region including the top of the spine beginning in the skull, the thoracic region spanning the torso, the lumbar region spanning the lower back, and the sacral region including the base of the spine ending with connection to the pelvic bone. With the exception of the first two cervical vertebrae, cushion-like discs separate adjacent vertebrae, i.e. intervertebral discs.

The stability of the vertebral column during compression and movement is maintained by the intervertebral discs. Each disc includes a gel-like center surrounded by a fibrous ring. The gel-like center, i.e. nucleus pulposus, provides strength such that the disc can absorb and distribute external loads and contains a mixture of type II-collagen dispersed in a proteoglycan matrix. The fibrous ring, or annulus fibrosus, provides stability during motion and contains laminated rings of type-I collagen. Thus, the annulus fibrosis and the nucleus pulposus are interdependent, as the annulus fibrosis contains the nucleus pulposus in place and the nucleus pulposus aligns the annulus fibrosus to accept and distribute external loads. The integrity of the composition and structure of the intervertebral disc is necessary to maintain normal functioning of the intervertebral disc.

Many factors can adversely alter the composition and structure of the intervertebral disc, such as normal physiological aging, mechanical injury/trauma, and/or disease, resulting in impairment or loss of disc function. For example, the content of proteoglycan n the nucleus pulposus declines with age, thus, it follows that the ability of the nucleus pulposus to absorb water concurrently declines. Therefore, in normal aging the disc progressively dehydrates, resulting in a decrease in disc height and possible de-lamination of the annulus fibrosus. Mechanical injury can tear the annulus fibrosis allowing the gel-like material of the nucleus pulposus to extrude into the spinal canal and compress neural elements. Growth of a spinal tumor can impinge upon the vertebrae and/or disc potentially compressing nerves.

Bones of the spine, and bony structures, generally, are susceptible to a variety of weaknesses that can affect their ability to provide support and structure. Weaknesses in bony structures have numerous potential causes, including degenerative diseases, tumors, fractures, and dislocations. Advances in medicine and engineering have provided doctors with a plurality of devices and techniques for alleviating or curing these weaknesses.

In some cases, the spinal column, in particular, requires additional support in order to address such weaknesses. One technique for providing support is to insert a spacer between adjacent vertebrae.

SUMMARY

In accordance with an embodiment of the disclosure, a spacer for separating bone of a joint may be provided. The spacer may comprise a first endplate configured to engage a first bone of the joint, and comprising a ramped surface; a tissue engaging subassembly disposed in a compartment of the first endplate; a second endplate configured to engage a second bone of the joint; and a frame subassembly that extends between the first endplate and the second endplate. The frame subassembly comprises a drive nut, a drive shaft coupled to the drive nut, a ramped carriage coupled to the drive shaft, wherein the ramped carriage comprises a ramped surface operable to engage the ramped surface of the first endplate, and an actuation bar coupled to the drive nut comprising a plate operable to engage the tissue engaging subassembly.

In accordance with an embodiment of the disclosure, another spacer for separating bone of a joint may be provided. The spacer may comprise a first endplate configured to engage a first bone of the joint, wherein the first endplate comprises a pair of spaced first endplate ramped surfaces. The spacer may comprise a first pair of tissue engaging subassemblies, wherein each of the tissue engaging subassemblies are pivotally coupled to the first endplate. The spacer may comprise a second endplate configured to engage a second bone of the joint, wherein the second endplate comprises a pair of spaced second endplate ramped surfaces. The spacer may comprise a second pair of tissue engaging subassemblies, wherein each of the tissue engaging subassemblies are pivotally coupled to the first endplate. The spacer may comprise a frame subassembly that extends between the first endplate and the second endplate. The frame subassembly comprise a drive nut at a proximate end of the spacer, wherein the drive nut comprises a head portion and an extension, wherein the extension comprises a threaded portion. The frame subassembly may comprise a drive shaft extending from the drive nut towards a distal end of the spacer, wherein a proximal end of the drive shaft is retained in a through bore of the drive nut. The frame subassembly may comprise a pair of ramped carriages that are spaced and threadingly coupled to the drive nut, wherein each of the ramped carriages comprises ramped surfaces operable to engage the second endplate ramped surfaces and the second endplate ramped surfaces. The frame subassembly may comprise an actuation bar coupled to the drive shaft. The actuation bar may comprise a base plate threadingly coupled to the threaded portion of the drive nut. The actuation bar may comprise a pair of opposing arms that extend from the base plate toward a distal end of the spacer, the opposing arms extending through the ramped carriages. The actuation bar may comprise plates disposed in spaced slots formed in each of the opposing arms of the actuation bar, wherein the plates are operable to engaging the first pair of tissue engaging subassemblies and the second pair of tissue engaging subassemblies.

In accordance with an embodiment of the disclosure, a method of separating bones of a joint may be provided. The method may comprise inserting a spacer between bones of the joint. The method may comprise rotating a drive shaft of the spacer to cause translation of at least ramped carriage disposed on the drive shaft, wherein the at least one ramped carriage slides along at least one ramped surface of a first endplate of the spacer to cause the first endplate to move in a direction away from a second endplate of the spacer. The method may comprise rotating a drive nut of the spacer to cause translation of a bar subassembly disposed between the first endplate and the second endplate such that at least one plate coupled to the frame engages at least one tissue engaging subassembly to cause the at least one tissue engaging subassembly to deploy through the first endplate.

BRIEF DESCRIPTION OF THE DRAWINGS

These drawings illustrate certain aspects of some examples of the present invention, and should not be used to limit or define the invention.

FIG. 1 is a perspective view of a spacer of the disclosure in a collapsed position;

FIG. 2 is a perspective view of the spacer of FIG. 1 in an expanded position;

FIG. 3 is a perspective view of the spacer of FIG. 1 with body tissue engaging projections deployed;

FIGS. 4 and 5 illustrate an actuation frame subassembly of the spacer of FIG. 1;

FIG. 11 illustrates a projection actuation bar of the drive subassembly of FIG. 7;

FIG. 12 is a cutaway view of a projection actuation bar of the drive subassembly of FIG. 7;

FIG. 18 illustrates a body tissue engaging projection subassembly of the spacer of FIG. 1;

FIG. 19 is an exploded view of a body tissue engaging projection subassembly of the spacer of FIG. 1;

FIG. 20 illustrates a base of the body tissue engaging projection subassembly of FIG. 18;

DETAILED DESCRIPTION

Figure 6:
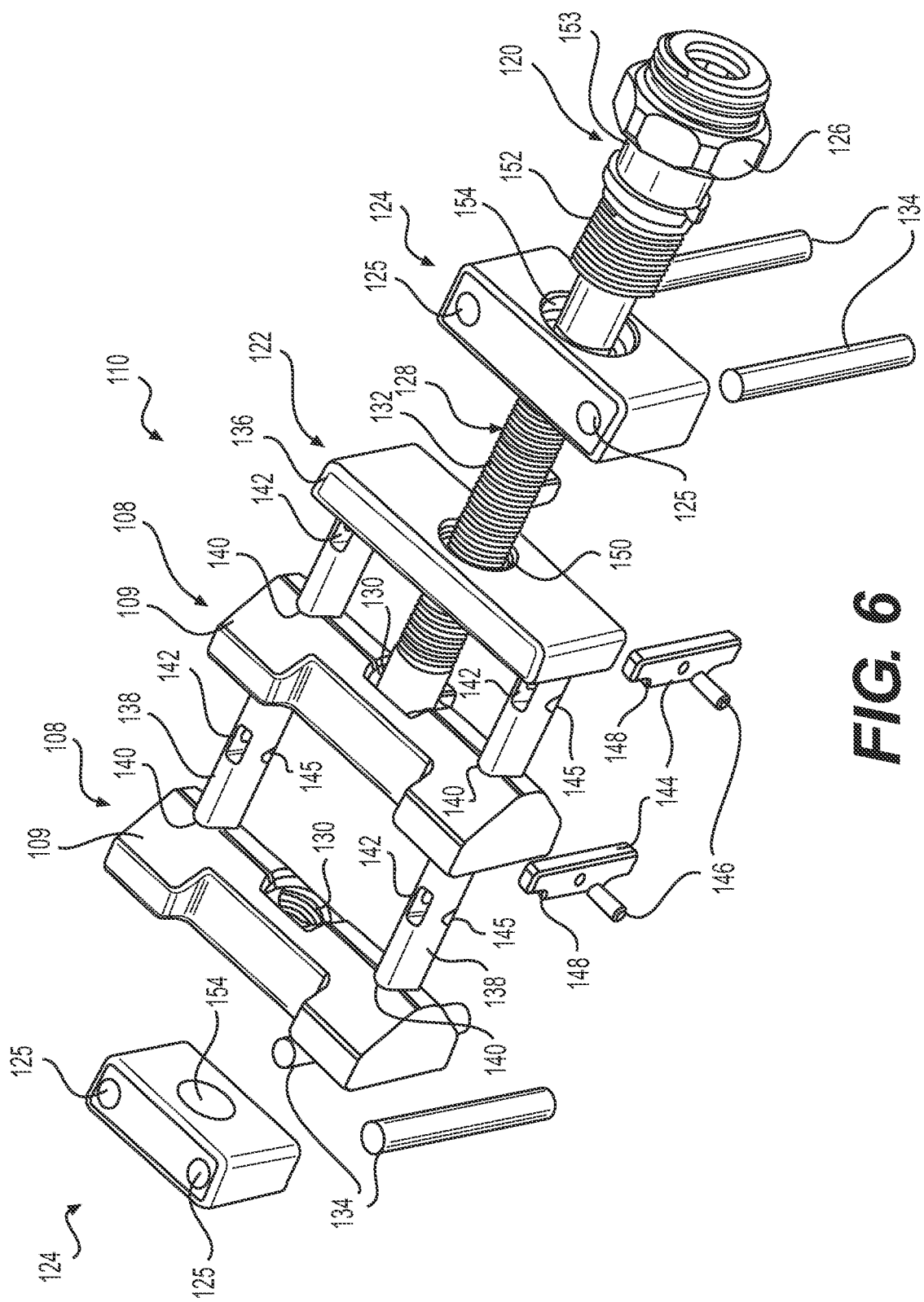
FIG. 6 is an exploded view of an actuation frame subassembly of the spacer of FIG. 1.

With reference to FIGS. 1-3, the disclosure provides a spacer 100 that is stabilized and has an adjustable height. The spacer is inserted between two adjacent bony surfaces to facilitate separation of the bones, and if desired, to promote the fusion of bony surfaces. Although intended to be useful with any adjacent bony surface in which fusion is desired, the spacer 100 is advantageously applied to insertion between two adjacent vertebral bodies in any section of the spine, including the cervical, thoracic, lumbar, and sacral vertebral sections. More than one spacer 100 may be implanted within the body, for example between successive or separated vertebrae, between adjacent vertebrae. The use of multiple spacers 100 is particularly advantageous for patients whose back pain is not limited to a localized area, or for patients whose localized damage has progressed to other areas of the spine.

The spacer 100 and methods for its insertion can be used in a treatment protocol for any of a wide variety of conditions in a patient involving diseased or damaged bony structures. The patient can be a human being. Additionally, it is contemplated that the spacer 100 may be useful in veterinary science for any animal having adjacent bony structures to be fused. The spacer 100 can collapse, for example, to approximately one half of an expanded size, as illustrated on FIG. 1, for example. When in this collapsed configuration, the spacer 100 can be inserted into a space through a small incision and narrow pathways, using appropriate minimally-invasive techniques, and can be positioned within the space between adjacent bones, and there expanded to a desired therapeutic height, as illustrated on FIG. 2, for example. The incision may be short, for example about one inch in length, which is smaller than the spacer 100 in an expanded configuration. If the desired position and/or expansion are not achieved, the spacer 100 can be collapsed, repositioned, and re-expanded in situ. Additionally, body tissue engaging projections 118 may be retracted during insertion and expansion of spacer 100. After the spacer 100 has been inserted and expanded, body tissue engaging projections 118 may be deployed, as shown on FIG. 3, for example.

Although the spacer 100 is exemplified herein for use in the spine, the spacer 100 is contemplated for fusion of any bony structures. While the spacers 100 are described herein using several varying embodiments, the spacers 100 are not limited to these embodiments. An element of one embodiment may be used in another embodiment, or an embodiment may not include all described elements.

With continued reference to FIGS. 1-3, embodiments of spacer 100 may include endplates 102, 104 having expansion ramps 106 mateable with moveable ramped carriages 108 on actuation frame subassembly 110. In the embodiment shown, endplates 102, 104 are symmetrical, and spacer 100 can be implanted with either endplate positioned superior with respect to the other. In other embodiments, they may be dissimilar, and a particular orientation may then be advantageous or necessary.

Spacer 100 forms a distal end 112 which may be inserted first into the body, and which can be tapered to facilitate insertion between body tissue, and a proximal end 114, to which a tool may be connected. Spacer 100 may be inserted into the body in a collapsed position shown on FIG. 1. Distal and proximal ends 112 and 114 define a longitudinal axis 116, extending therebetween. To expand spacer 100, ramped carriages 108 may be displaced relative to endplates 102, 104 causing expansion ramps 106 to slide along ramped carriages 108, thereby moving endplates 102, 104 relatively apart such that a height of spacer 100 may be increased. FIG. 2 illustrates the spacer 100 in an expanded position. As seen on FIG. 3, spacer 100 further includes body tissue engaging projections 118. The body tissue engaging projections 118 may be retracted during insertion and expansion of spacer 100. After the spacer 100 has been inserted and expanded, body tissue engaging projections 118 may be deployed. The body tissue engaging projections 118 may be deployed to engage adjacent tissue (e.g., endplates), for example, to fixate the spacer 100 in place. Advantageously, engagement of adjacent tissue with body tissue engaging projections 118 may prevent migration and/or tipping spacer 100 prior to fusion occurring.

Turning now to FIGS. 4-6, actuation frame subassembly 110 is illustrated in more detail in accordance with embodiments of the present disclosure. Actuation frame subassembly 110 may extend between endplates 104, 104. As illustrated, actuation frame subassembly 110 may comprise ramped carriages 108, drive subassembly 120, projection actuation bar 122, and retainer blocks 124. In the illustrated embodiment, drive subassembly 120 comprises drive nut 126 and drive shaft 128. Ramped carriages 108 may be displaced relative to endplates 102, 104 (e.g., shown on FIGS. 1-3) by rotation of drive shaft 128. In some embodiments, rotation of drive shaft 128 may cause ramped carriages 108 to translate a path along longitudinal axis 116 of spacer 100. Ramped carriages 108 may each have a through bore 130 (best seen on FIG. 6) which may be threadedly coupled to a threaded portion 132 of drive shaft 128. Ramped carriages 108 may each comprise ramped surfaces 109 that engage the corresponding expansion ramps 106 of endplates 102, 104 (e.g., shown on FIGS. 103). In some embodiments, each ramped carriage 108 may comprise a pair of ramped surfaces 109 on opposite sides of the ramped carriage 108. In some embodiments, one or more guide elements (e.g., guide pins 134 on FIGS. 4-7) may be provided to prevent endplates 102, 104 from moving along longitudinal axis 116 along with ramped carriages 108, thereby causing ramped carriages 108 and expansion ramps 106 to be moved relative to one another, expanding or contracting spacer 100. While FIGS. 4-6 illustrate guides pins 134 as one-piece pins, each of guide pins 134 may be multi-piece.

In some embodiments, projection actuation bar 122 may comprise base plate 136 and arms 138. In the illustrated embodiment, arms 138 extend from base plate 136 in the direction of distal end 112 of spacer 100. As illustrated, arms 138 may extend substantially parallel and be generally opposed to one another. In some embodiments, arms 138 may extend through corresponding through bores 140 in ramped carriages 108. In the illustrated embodiment, slots 142 may be formed in arms 138. Any number of slots 142 may be formed in arms 138. In the illustrated embodiment, each of the arms 138 includes a pair of slots 142. In some embodiments, one of the slots 142 may be disposed in each arm 138 between the ramped carriages 108 while the other of the slots 142 may be disposed between base plate 136 and one of the ramped carriages 108. Plates 144 may be secured in each of the slots 142. In the illustrated embodiments, pins 146 may secure plates 144 in slots 142. In some embodiments, plates 144 may project from either end of slots 142. As best seen on FIG. 6, pins 146 may extend through holes 145 in arms 138. While FIGS. 4-6 illustrate plates 144 as one-piece plates, each of plates 144 may be multi-piece. Additionally, each end of plates 144 may contain a notch 148 (best seen on FIG. 6).

In some embodiments, projection actuation bar 122 may be displaced relative to endplates 102, 104 (e.g., shown on FIGS. 1-3) by rotation of drive nut 126. As best seen on FIG. 6, base plate 136 may contain a through bore 150, which may be threadedly coupled to a threaded portion 152 of an extension 153 from drive nut 126. In accordance with present embodiments, rotation of drive nut 126 may cause projection actuation bar 122 to translate along longitudinal axis 116 of spacer. Because arms 138 may extend through ramped carriages 108, rotational movement of drive nut 126 may cause translation of projection actuation bar 122 as ramped carriages 108 prevent rotation of projection actuation bar 122.

In some embodiments, actuation frame subassembly 110 may comprise a pair of retainer blocks 124. Guide pins 134 may be disposed in retainer blocks 124. As illustrated, guide pins 134 may project from either end of retainer blocks 124. In some embodiments, guide pins 134 may be placed in corresponding openings 125 in retainer blocks 124, as seen on FIG. 6. The retainer blocks 124 may each have a through bore 154. In the illustrated embodiment, one of the retainer blocks 124 may be disposed on extension 153 of drive nut, wherein plate 106 is disposed between that particular retainer block 124 and ramped carriages 108. The other retainer block 124 may be disposed at an opposite end of drive subassembly 120 on the drive shaft 128, wherein ramped carriages and plate 106 may be disposed between the retainer blocks 124.

Figure 7:
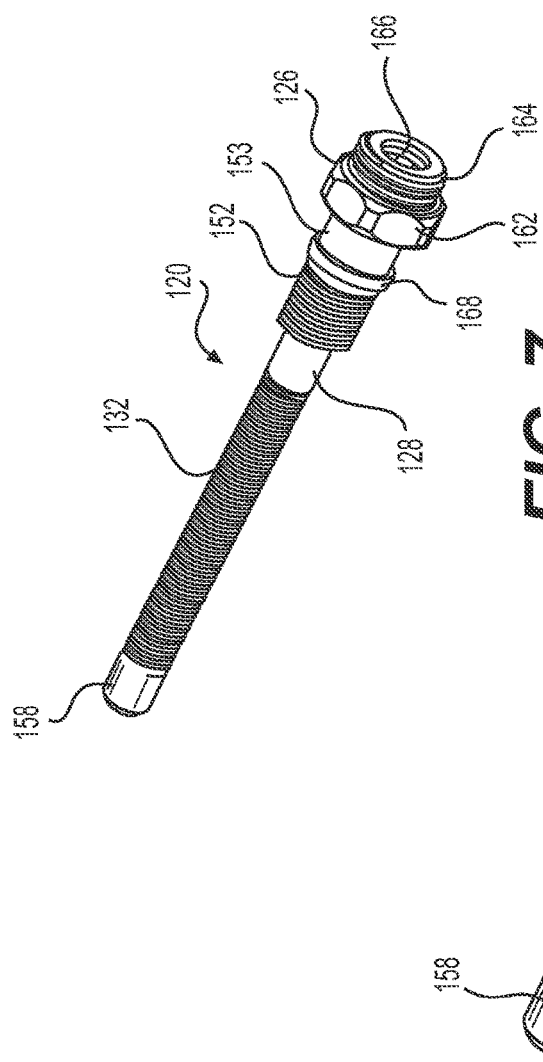
FIG. 7 illustrates a drive subassembly of the spacer of FIG. 1.
Figure 8:
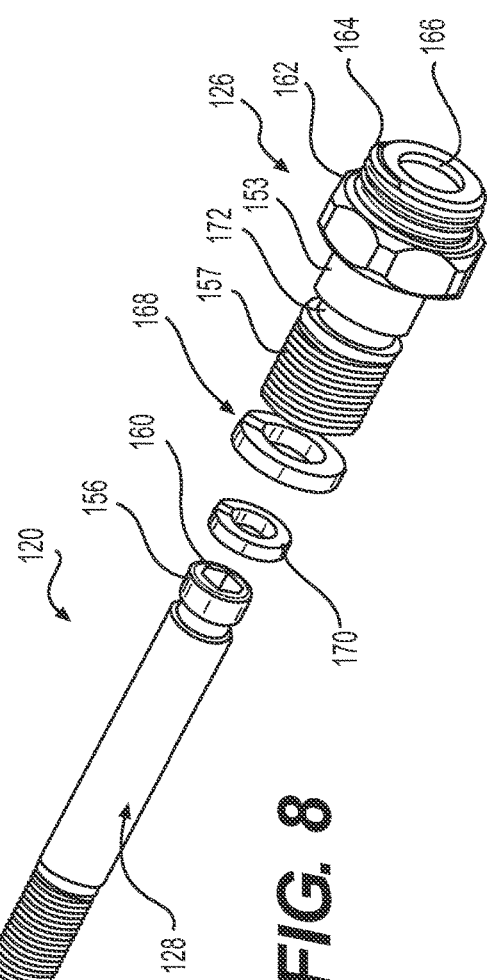
FIG. 8 illustrates an exploded view of a drive subassembly of the spacer of FIG. 1.

Turning now to FIGS. 7 and 8, drive subassembly 120 is illustrated in more detail in accordance with embodiments of the present invention. As illustrated, drive assembly 120 includes a drive nut 126 and a drive shaft 128. In the illustrated embodiment, drive shaft 128 includes a threaded portion 132. Drive shaft 128 may include a proximal end 156 and a distal end 158. Drive shaft 128 may further include a tool engagement portion 160 to which a tool may be connected for rotation of drive shaft 128 such that ramped carriages 108 may be withdrawn or advanced. As illustrated, the tool engagement portion 160 may be disposed at proximal end 156. In the illustrated embodiment, tool engagement portion 160 is in the form of a hexagonal opening, but it should be understood that other tool engagement types or shapes may be used as would be understood by those ordinary skill in the art.

Figure 9:
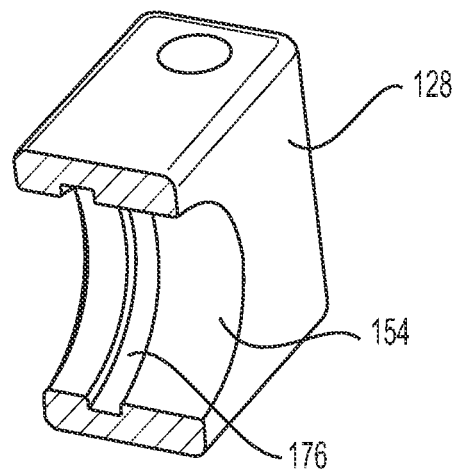
FIG. 9 is a cutaway view of a drive screw of the drive subassembly of FIG. 7.

With additional reference to FIG. 9, drive nut 126 may include a head portion 162 and an extension 152. As illustrated, extension 152 may include a threaded portion 153. An insertion tool (not shown) may threadably engage threaded portion 153 and thus engage spacer 100 so that spacer 100 can be retained during insertion. In the illustrated embodiment, a threaded end 164 may extend from head portion 162 in an opposite direction from extension 152. A tool (not shown) may interact with head portion 162 to cause rotation of drive nut 126 so that projection actuation bar 122 (e.g., shown on FIGS. 4-6) may be withdrawn or advanced.

Embodiments of drive nut 126 may also include a through bore 166. In some embodiments, drive nut may further include first ring 168 and second ring 170, which may both be in the form of a c-ring or other suitable device. In some embodiments, first ring 168 and second ring 170 may be compressible. In the illustrated embodiment, first ring 168 may be retained in a groove 172 (best seen on FIGS. 8 and 9) formed in extension 152. In the illustrated embodiment, second ring 170 may be retained in an internal groove 174 formed in through bore 166 (best seen on FIG. 9). Proximal end 156 of drive shaft 128 may be inserted into through bore 166. In some embodiments, second ring 170 may be disposed on groove 176 of drive shaft 128 during insertion into through bore 166 and expand to engage internal groove 174, thus securing drive shaft 128 in through bore 166.

Figure 10:
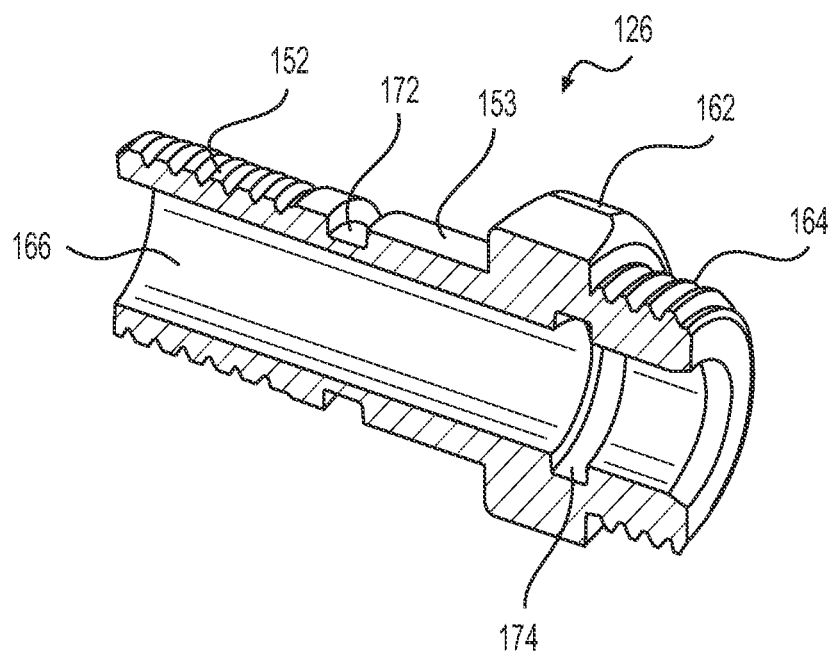
FIG. 10 is a cutaway view of a retainer block of the drive subassembly of FIG. 7.

With additional reference to FIG. 10, a cutaway view of one of the retainer blocks 124 is illustrated. As previously described, retainer blocks 124 may include a through bore 154. In the illustrated embodiment, through bore 154 includes an internal groove 176. First ring 168 disposed on drive nut 126 may engage internal groove 176 to retain one of the retainer blocks 124 on extension 153 of drive nut 126.

Turning now to FIGS. 10 and 11, projection actuation bar 122 is illustrated in more detail in accordance with present embodiments. In some embodiments, projection actuation bar 122 may comprise base plate 136 and arms 138. In the illustrated embodiment, base plate 136 may be in the form of a rectangular block with a proximal facing surface 178 and a distal facing surface 180. A through bore 150 may be formed in base plate 136 that extends from proximal facing surface 178 to distal facing surface 180. In some embodiments, through bore 150 may contain threads 182, as illustrated on FIGS. 10 and 11. As best seen on FIG. 6, threaded portion 152 of drive nut 120 may threadingly engage threads 182 of through bore 150 such that rotation of drive nut 120 causes projection actuation bar 122 to translate along the longitudinal axis 116 of spacer 100. As illustrated, through bore 150 may be located generally in the center of proximal facing surface 178, but through bore 150 may be placed in other suitable locations. In some embodiments, arms 138 may extend from distal facing surface 180 of base plate 136. Arms 138 may generally be parallel and opposed to one another. As illustrated, rods 138 may be cylindrical in shape, but other suitable shapes may be used included those with rectangular, square, elliptical or otherwise formed cross-sections. In the illustrated embodiments, slots 142 may be formed in arms 138. Slots 142 may extend vertically and generally perpendicular to the longitudinal axis of the arms 138. As illustrated, a pair of slots 142 may be formed in each of the arms 138. In some embodiments, holes 145 may be formed in arms 138 that intersect slots 142. As illustrated, holes 145 may each extend horizontally through arms 138 to intersect slots 142.

Figure 13:
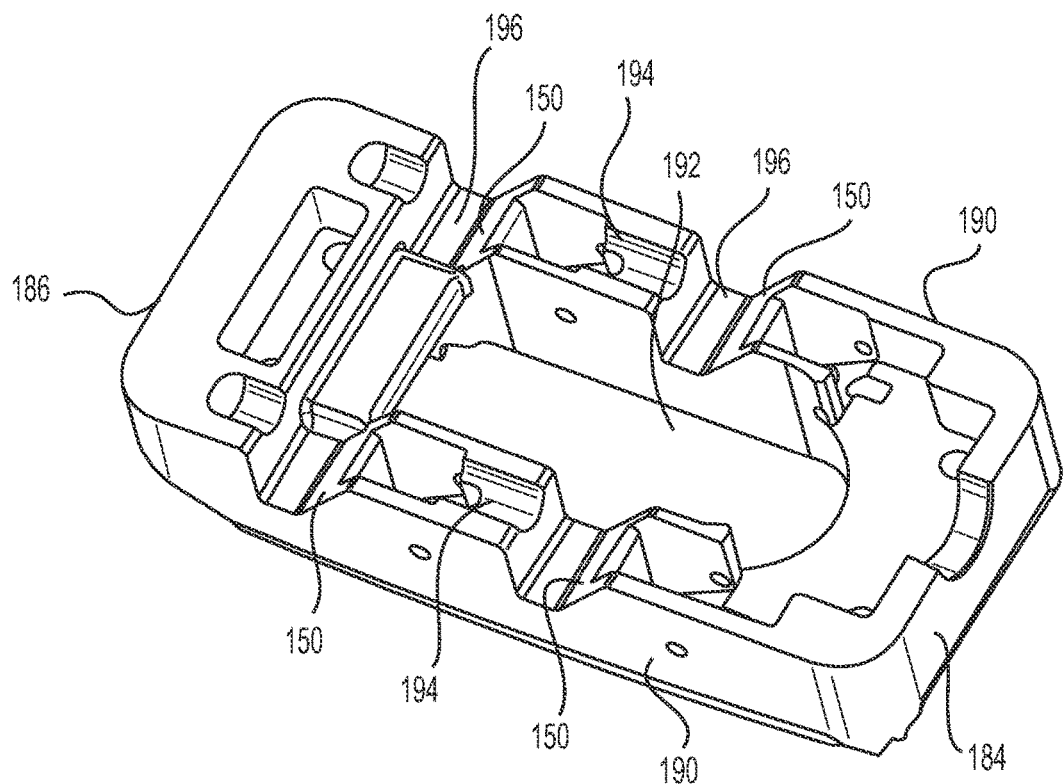
FIGS. 13 and 14 are alternate views of an endplate of the spacer of FIG. 1.

Embodiments of endplates 102, 104 will now be described in more detail with reference to FIGS. 13-15. The following description is for endplate 102; however, it should be understood that endplates 102 and 104 may be symmetrical so the description may equally apply to endplate 104. Endplate 102 may have a proximal end 184 and a distal end 186. As best seen on FIG. 14, endplate 102 may further comprise an outer facing surface 188 connecting proximal end 184 and distal end 186. As illustrated, lateral sides 190 may extend downwardly from outer facing surface 188. In some embodiments, expansion ramps 106 may be formed in lateral sides 190. As illustrated, each of the expansion ramps 106 may comprise a pair of expansion ramps 106. The expansion ramps 106 may be at an incline with respect to longitudinal axis 116 of spacer 100. It should be understood that the number, spacing, incline, and arrangement of expansion ramps 106 may vary as desired for a particular application. By way of example, expansion ramps 106 and/or ramped carriages 108 may be of differing height within spacer 100, whereby endplates 102, 104 may mutually separate at different rates at distal and proximal ends 112, 114, whereby an angular disposition of adjacent bones may be changed, for example to correct lordosis or scoliosis. As previously described, ramped carriages 108 (e.g., FIG. 1) may engage expansion ramps 106. In some embodiments, each of lateral sides 190 may also have an arm housing 194 formed therein in which arms 138 (e.g., FIG. 11) of projection actuation bar 122 may be disposed. In some embodiments, each of lateral sides 190 may also have cutouts 196. Cutouts 196 may be sized to receive ramped carriages 108. In the illustrated embodiment, expansion ramps 106 may be formed in cutouts 196. In some embodiments, endplate 102 may further comprise a cutout 198 in proximal end. Cutout 198 may be sized to receive extension 153 of drive nut 120.

In some embodiments, endplate 102 may further comprise a through opening 192. The through opening 192, in an exemplary embodiment, may be sized to receive bone graft or similar bone growth inducing material and further allow the bone graft or similar bone growth inducing material to be packed in a central opening 194 in actuation frame subassembly 110.

Endplates 102, 104 may additionally, or alternatively, be resilient, so that they may conform to bony surfaces, forming a more stable support platform. Accordingly, endplates 102, 104 can be fabricated from a polymeric material, a naturally resilient material, or a resilient metal, for example a shape memory alloy, or any other resilient biocompatible material of sufficient strength and durability for separating bones within the body.

Figure 14:
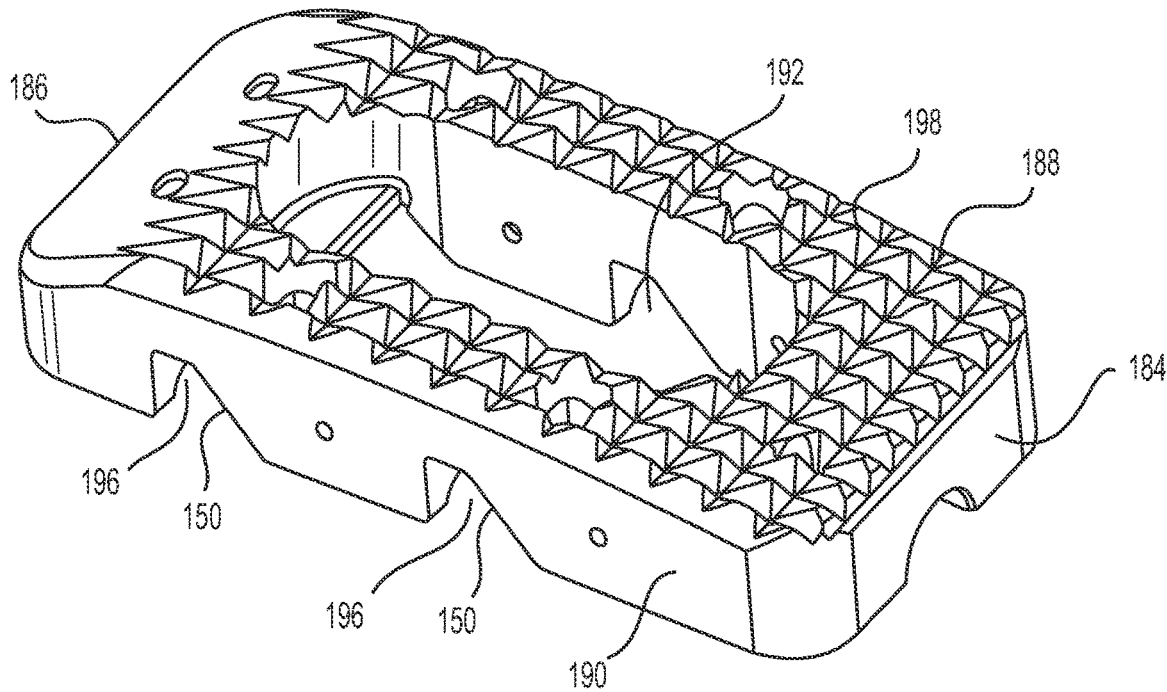
Figure 15:
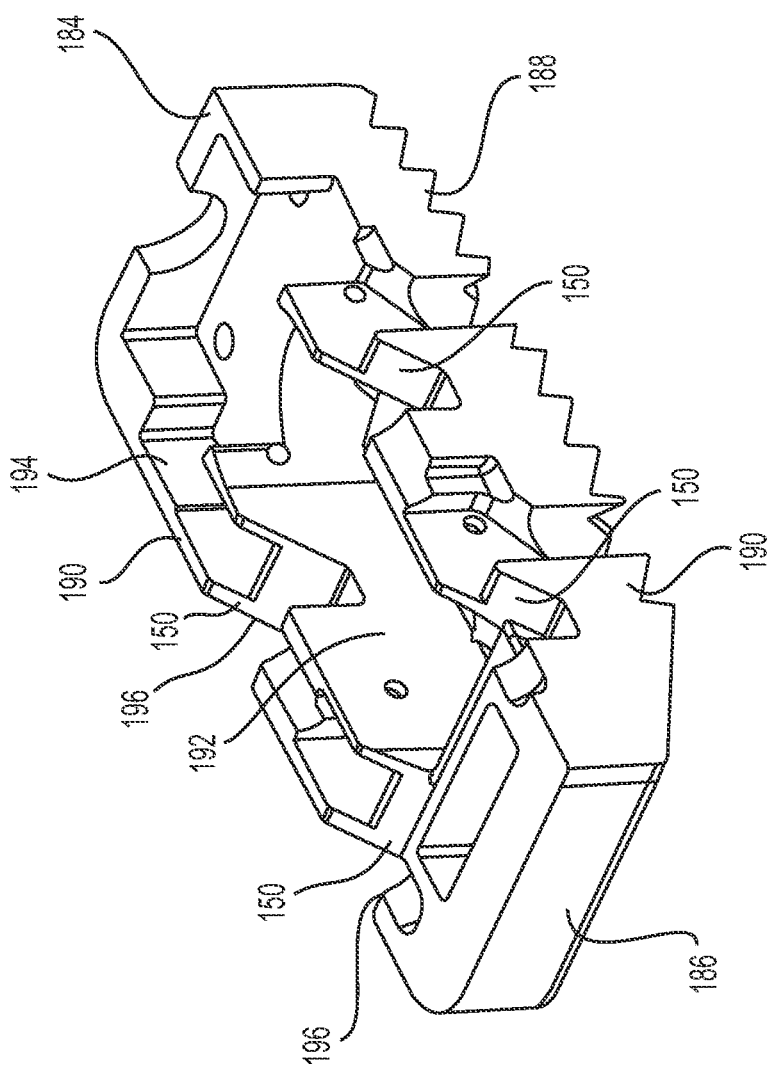
FIG. 15 is a cutaway view of an endplate of the spacer of FIG. 1.

As illustrated in FIG. 14, upper facing surface 188 of endplate 102 may be flat and generally planar to allow the upper facing surface 188 to engage with the adjacent vertebral body. In alternative embodiments (not shown), upper facing surface 188 can be curved convexly or concavely to allow for a greater or lesser degree of engagement with the adjacent vertebral body. It is also contemplated that the upper facing surface 188 can be generally planar but includes a generally straight ramped surface or a curved ramped surface. The ramped surface may allow for engagement with the adjacent vertebral body 2 in a lordotic fashion. Turning back to FIG. 14, in an exemplary embodiment, the upper facing surface 188 includes texturing 198 to aid in gripping the adjacent vertebral bodies. Although not limited to the following, the texturing can include teeth, ridges, friction increasing elements, keels, or gripping or purchasing projections.

Figure 16:
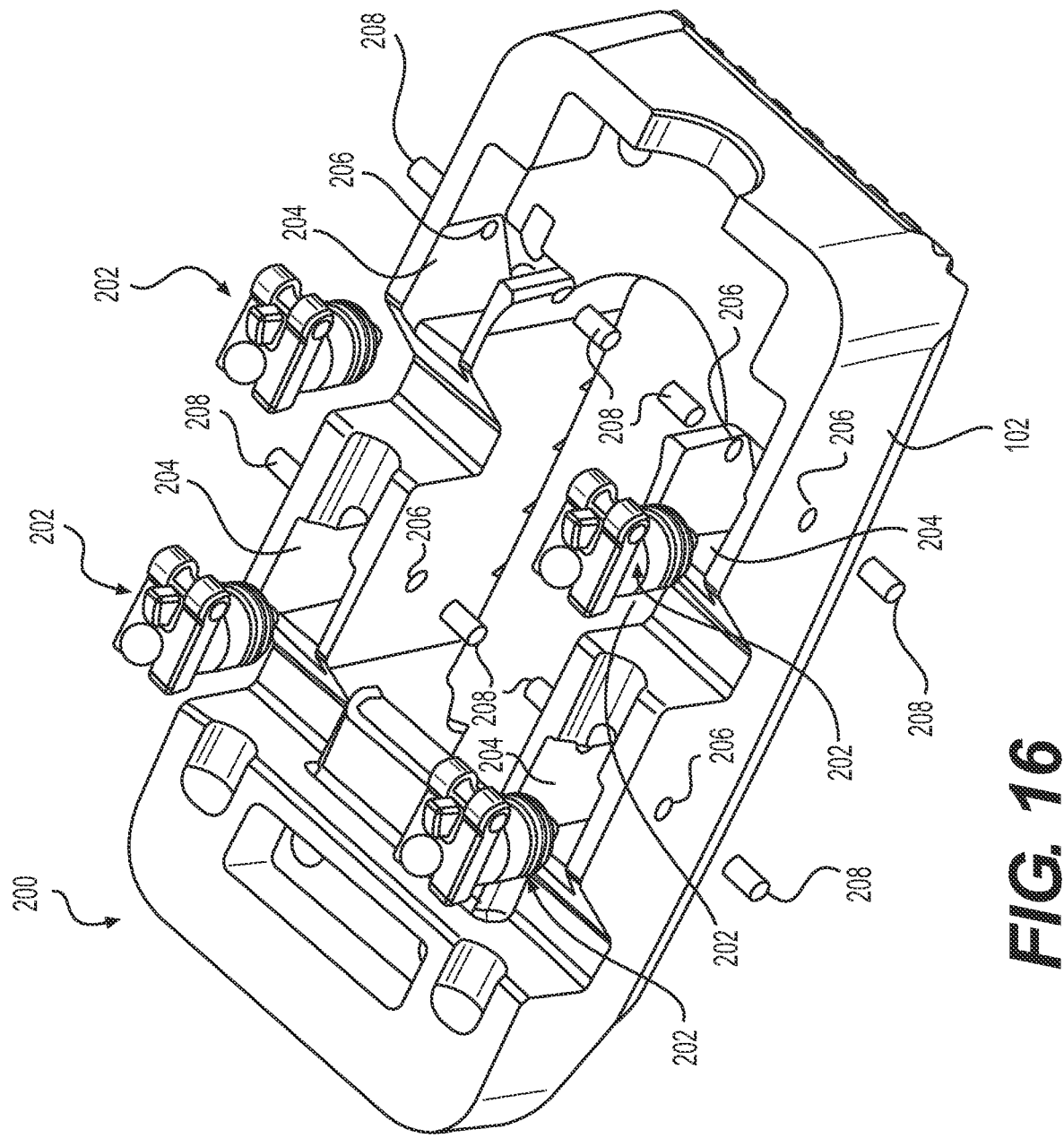
FIG. 16 is an exploded view of an endplate subassembly of the spacer of FIG. 1.
Figure 17:
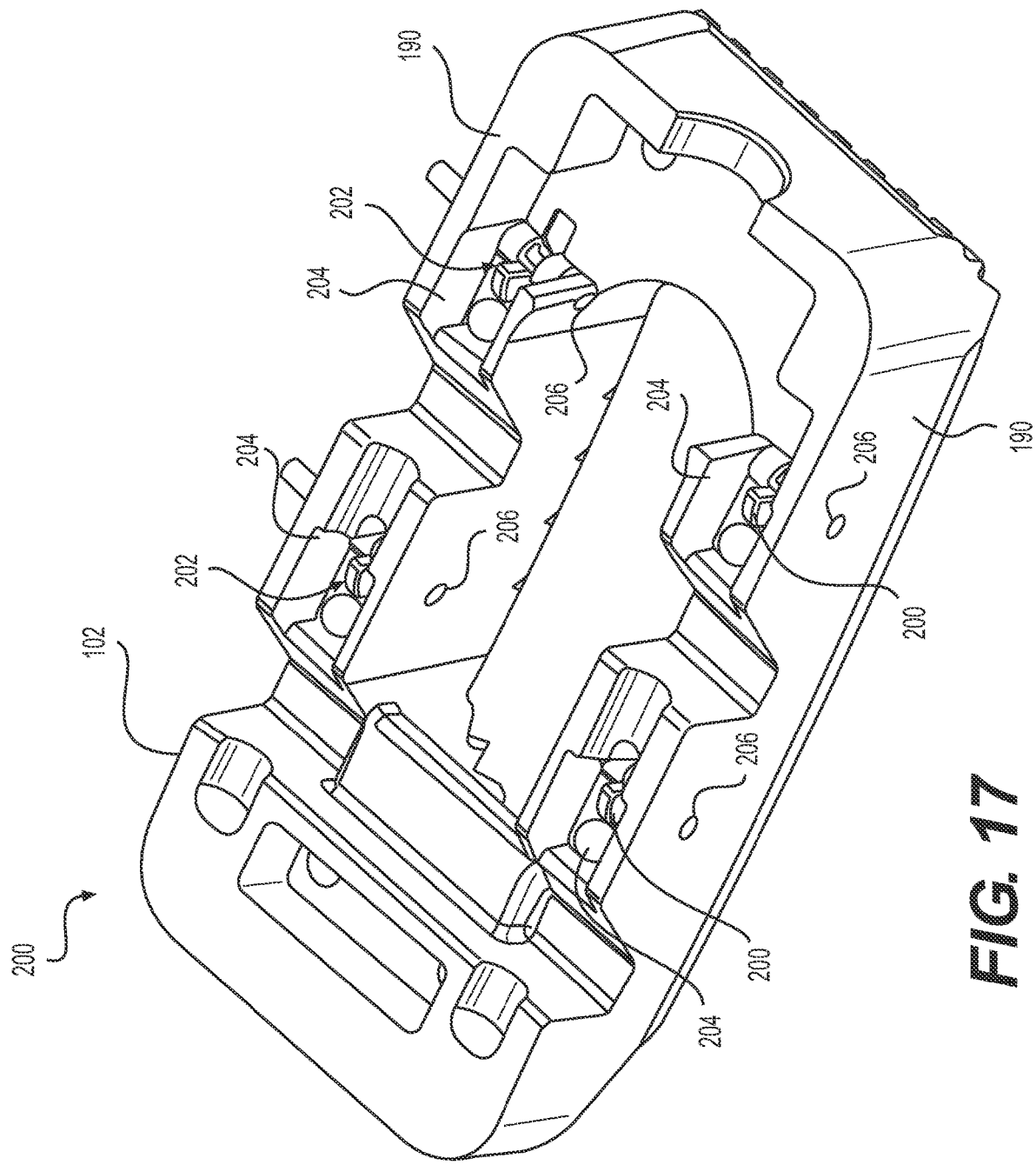
FIG. 17 illustrates an endplate subassembly of the spacer of FIG. 1.

With reference now to FIGS. 16 and 17, an endplate subassembly 200 is illustrated in more detail in accordance with embodiments of the present invention. In some embodiments, endplate subassembly 200 may comprise an endplate 102 and body tissue engaging projection subassemblies 202. While FIGS. 16 and 17 illustrated endplate 102, it should be understood that the description herein with respect to endplate subassembly 200 should apply equally to both of the endplates 102, 104. As best seen on FIGS. 16 and 17, compartments 204 may be formed in lateral sides 190. Compartments 204 may each be sized and configured to hold one of the body tissue engaging projection subassemblies 202. The lateral sides 190 may include holes 206. Pivot pins 208 may pass through the holes 206 to pivotally couple the body tissue engaging projection subassemblies 202 in compartments 204. The pivot pins 208 may define a pivot axis about which the body tissue engaging projection subassemblies 202 may be rotated. While the pivot pins 208 for each of the body tissue engaging projection subassemblies 202 is shown as being comprised of two or more parts, it should be understood that the pivot pins 208 may comprise more or less than two parts, for example, unitary pins may be used.

Embodiments of the body tissue engaging projection subassemblies 202 will now be described in more detail with respect to FIGS. 18-19. In the illustrated embodiment, tissue engaging projection assembly 202 includes base 210 and projection member 212. In some embodiments, projection member 212 may comprise a tissue engaging end 214 and a stop 216. Embodiments may further include post 218 that interconnects tissue engaging end 214 and stop 216. While tissue engaging end 214 is show in the form of a conical spike, it should be understood that different shaped tissue engaging ends may be used, including pyramid shaped ends and other pointed protrusions. In operation, the tissue engaging end 214 may engage an adjacent vertebral body to stabilize the spacer 100. In the illustrated embodiment, stop 216 is in the form of a ball. However, differently shaped stops may be used that may be suitable for securing projection member 212 to base 210.

With additional reference to FIG. 20, base 210 of tissue engaging projection subassembly 202 will now be described in more detail in accordance with embodiments of the present invention. In the illustrated embodiment, base 210 may comprise an outward facing surface 220 and an inward facing surface 222. In some embodiments, outward facing surface 220 and inward facing surface 222 may extend between first end 224 and second end 226. A channel 228 may be formed in base 210. Channel 228 may extend from outward facing surface 220 to inward facing surface 222. A sloping edge 230 may extend around channel 228 at inward facing surface 222. As illustrated, channel 228 may be generally u-shaped and extend to first end 224. Post 218 of projection member 212 may be received in channel 228. Stop 216 may be positioned on one side of base 210 while tissue engaging end 214 may be positioned on the other side of base 210. In this manner, projection member 212 may be pivotally coupled to base 210. At second end 226, base 210 may comprise a cylindrical-shaped section 232 in which an opening 234 is formed for receiving a pivot pin 208 (e.g., shown on FIG. 16). Opening 234 may form a pivot point about which base 210 may pivot. As best seen on FIG. 20, base 210 may further include a downward projection 236. Downward projection 236 may engage plate 144 of projection actuation bar 122 (e.g., shown on FIG. 6).

Figure 21:
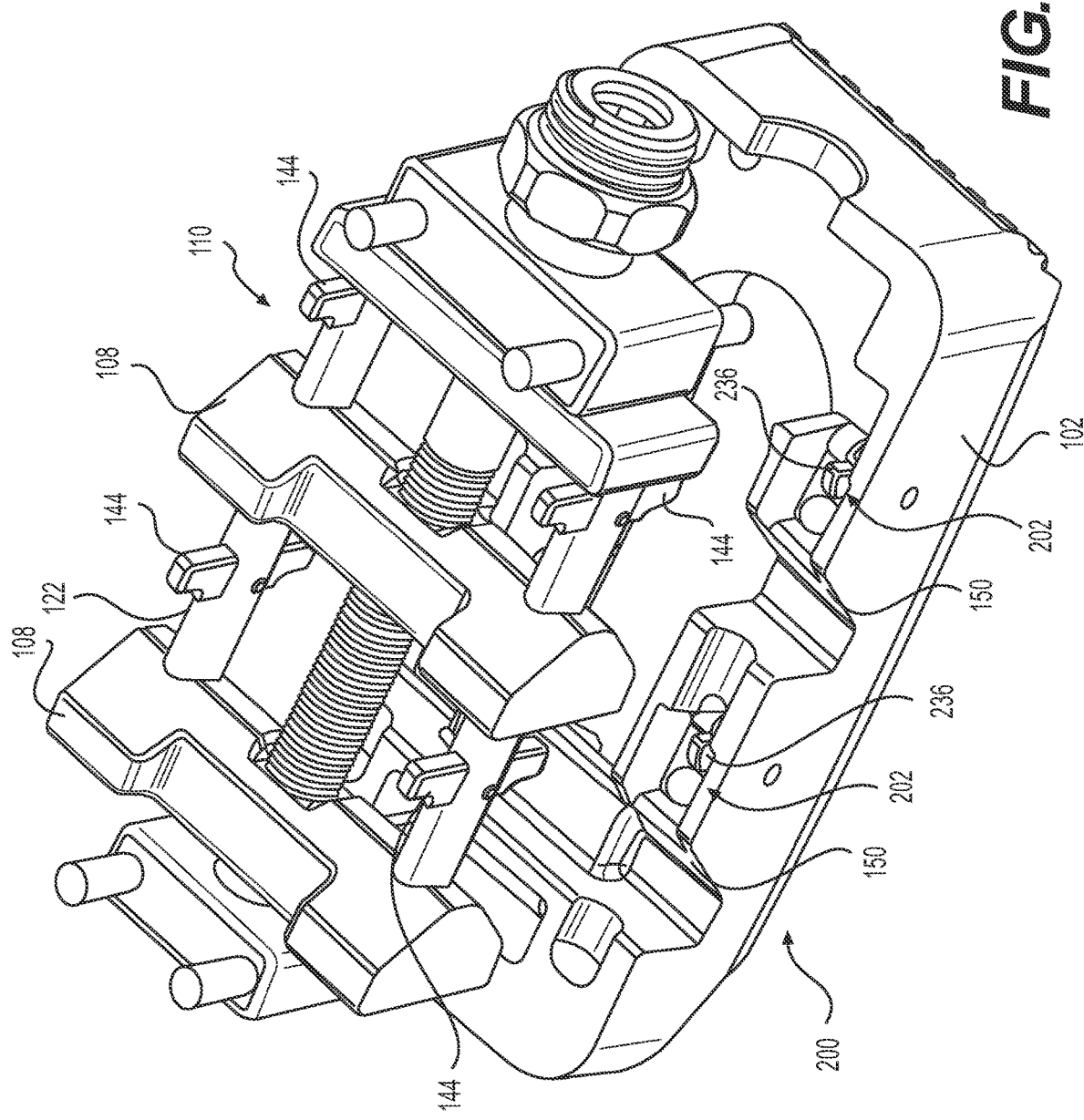
FIG. 21 illustrates positioning of the actuation frame subassembly with the endplate subassembly.
Figure 22:
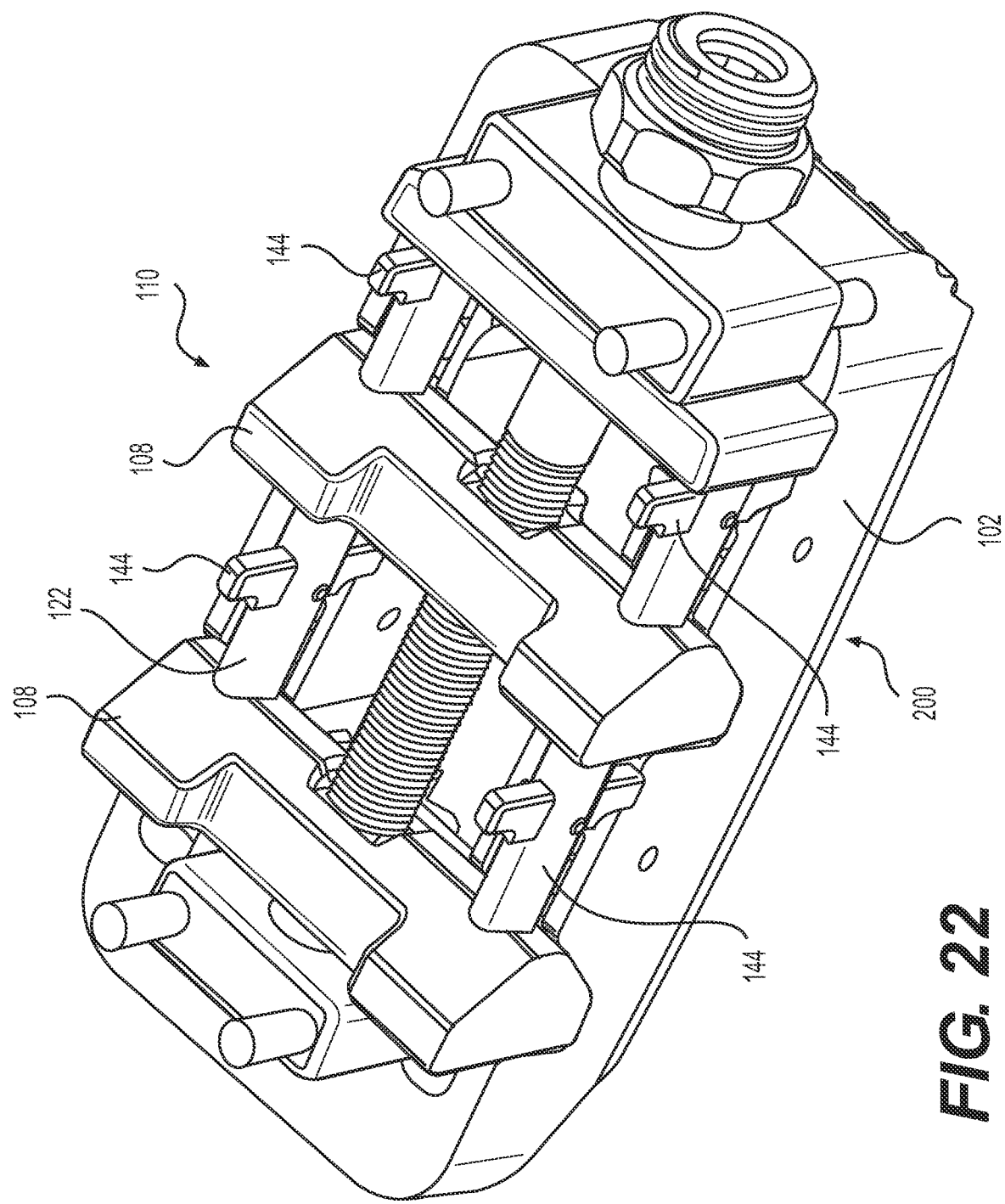
FIG. 22 illustrates positioning the endplate subassembly assembled with the actuation frame subassembly.

With reference now to FIGS. 21 and 22, assembly of actuation frame subassembly 110 to endplate subassembly 200 is illustrated in accordance with embodiments of the present invention. In some embodiments, actuation frame subassembly 110 may be positioned in endplate subassembly 220. Embodiments may include disposing ramped carriages 108 in cutouts 196 of endplate 102 such that ramped carriages 108 engage lift ramps 150. Additionally, actuation frame subassembly 110 may be positioned such that plates 144 of projection actuation bar 122 may engage downward projections 236 of tissue engaging projection subassemblies 202.

Figure 23:
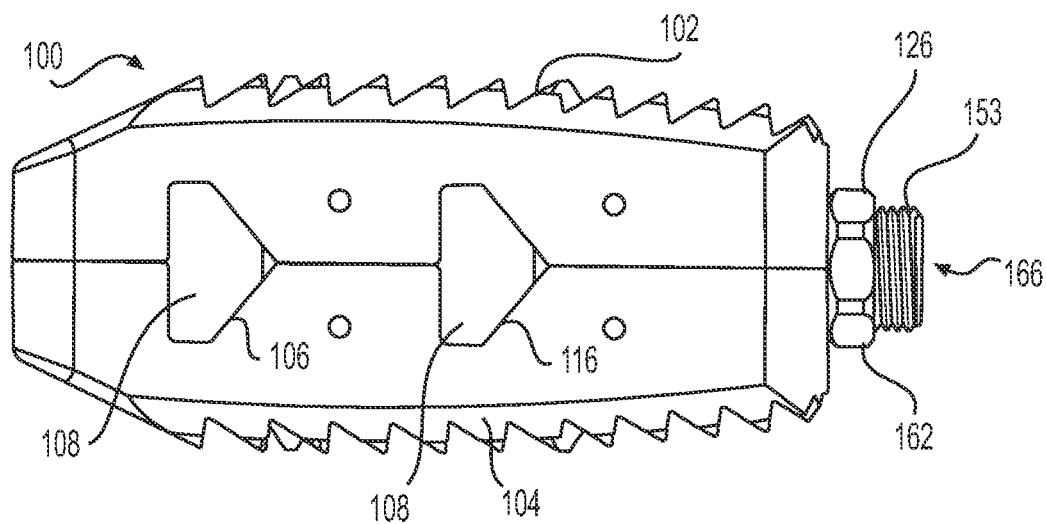
FIG. 23 is a side view of the spacer of FIG. 1 in a collapsed position.
Figure 24:
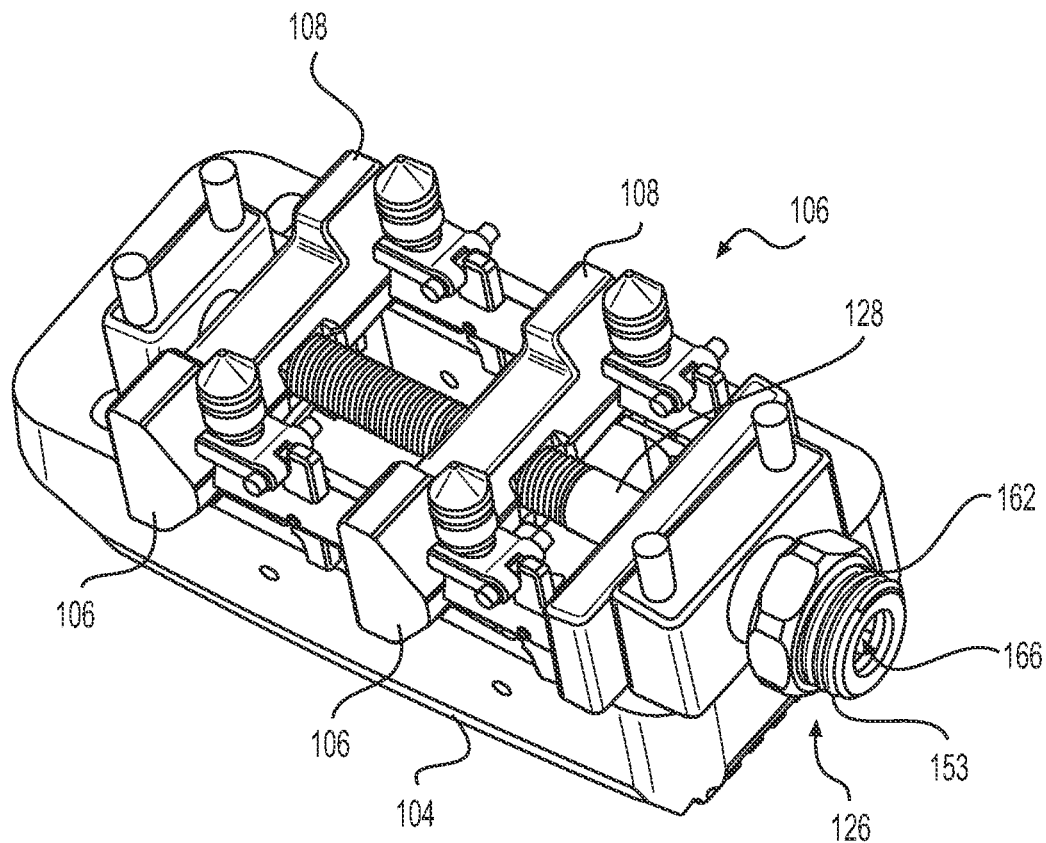
FIG. 24 is a cutaway view of the spacer of FIG. 1 in a collapsed position.
Figure 25:
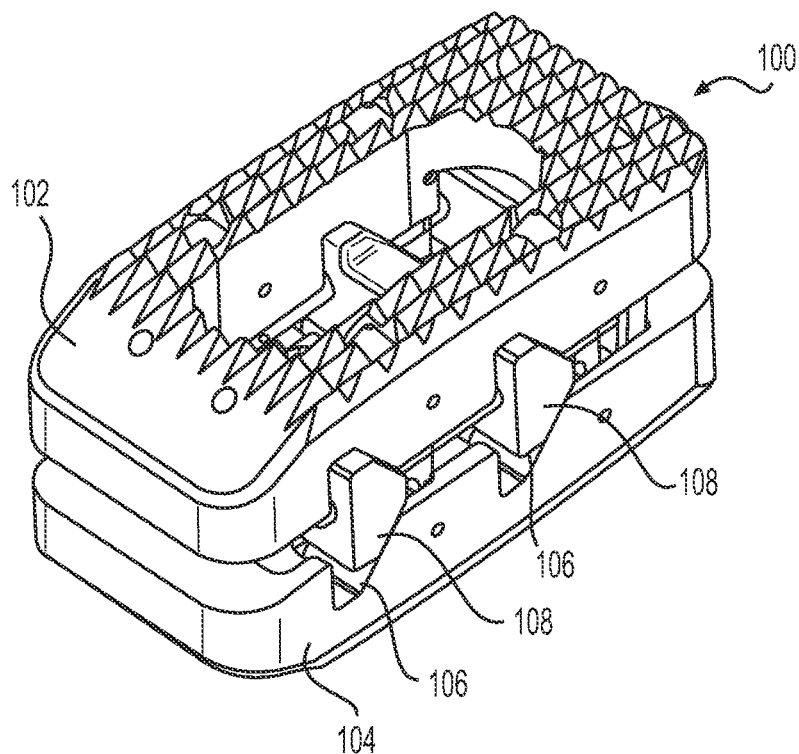
FIG. 25 is a perspective view of the spacer of FIG. 1 in an expanded position.
Figure 26:
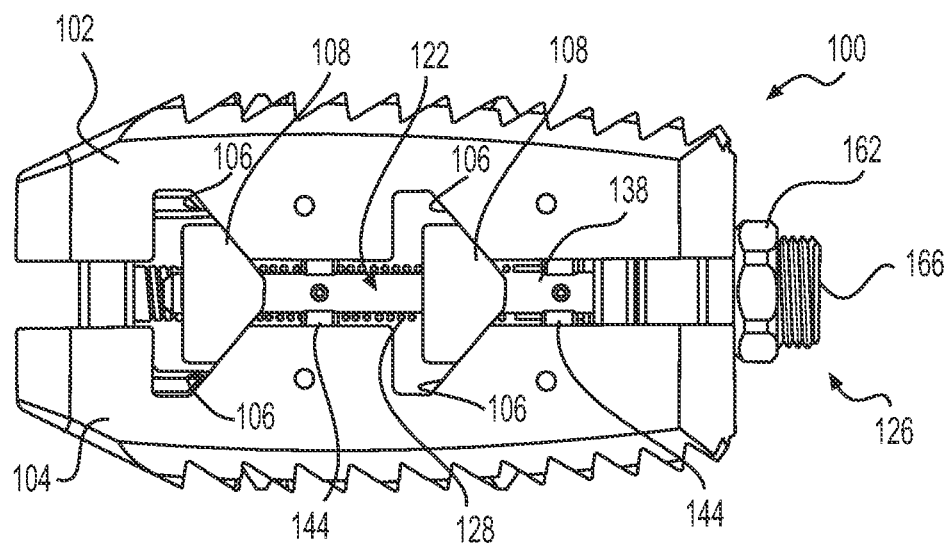
FIG. 26 is a side view of the spacer of FIG. 1 in an expanded position.
Figure 27:
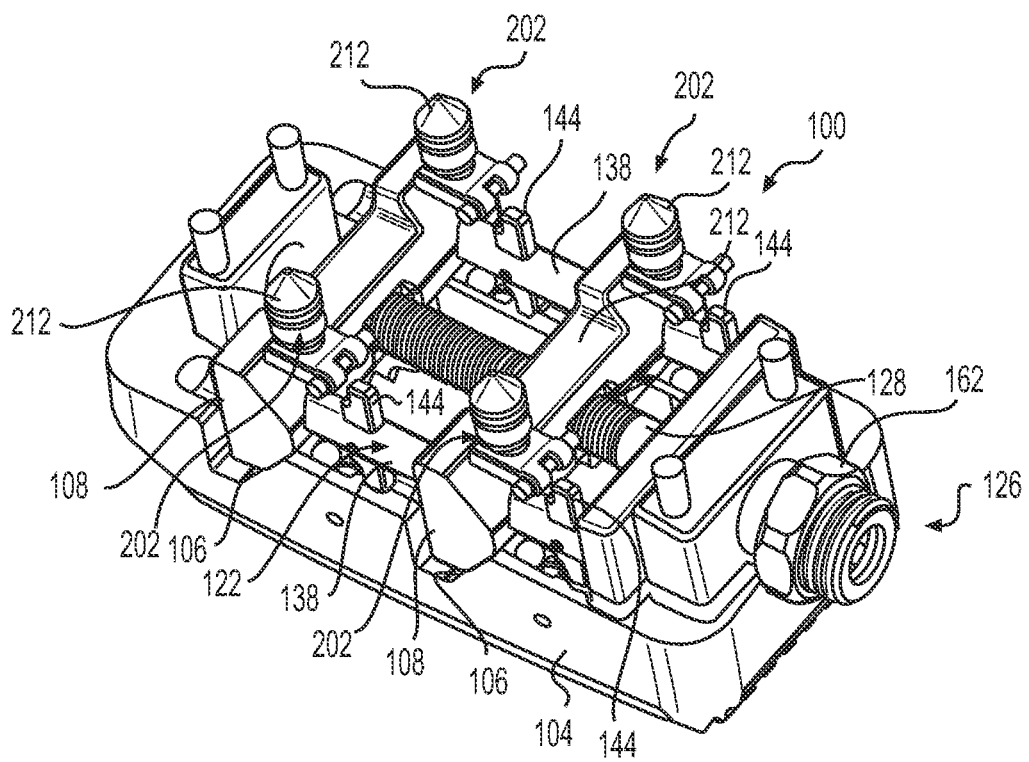
FIGS. 27 and 28 are cutaway views of the spacer of FIG. 1 in an expanded position.
Figure 28:
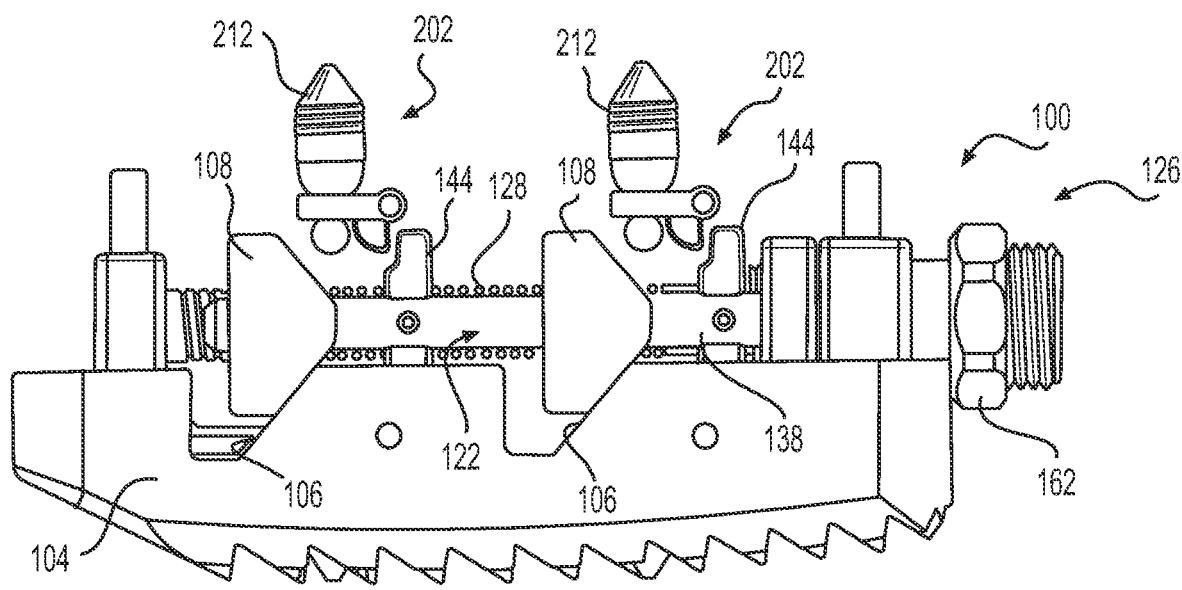
Figure 29:
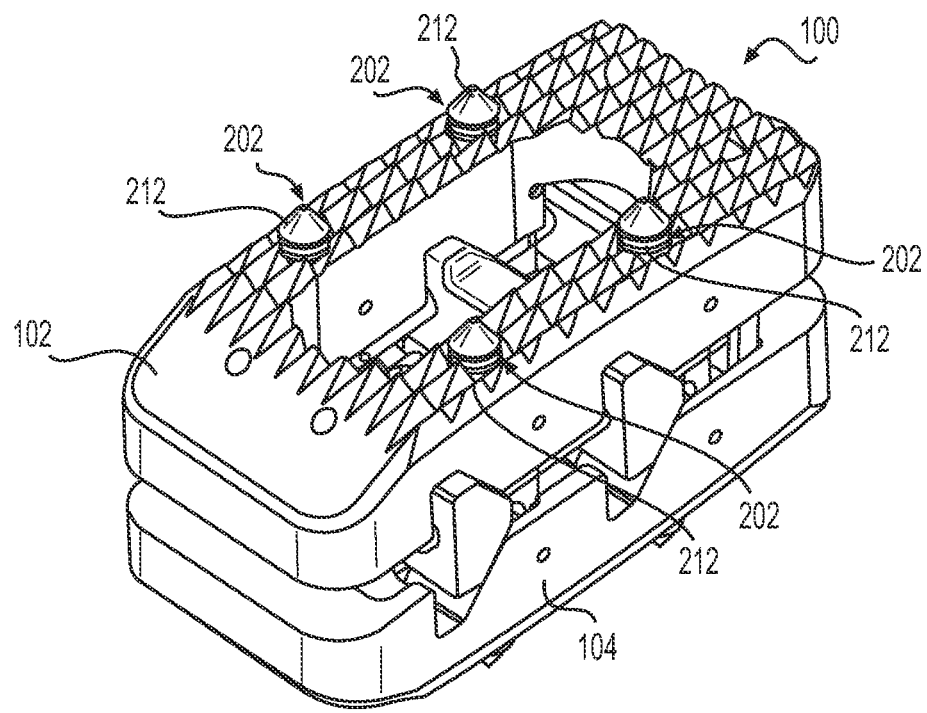
FIG. 29 is a perspective view of the spacer of FIG. 1 with body tissue engaging projections deployed.
Figure 30:
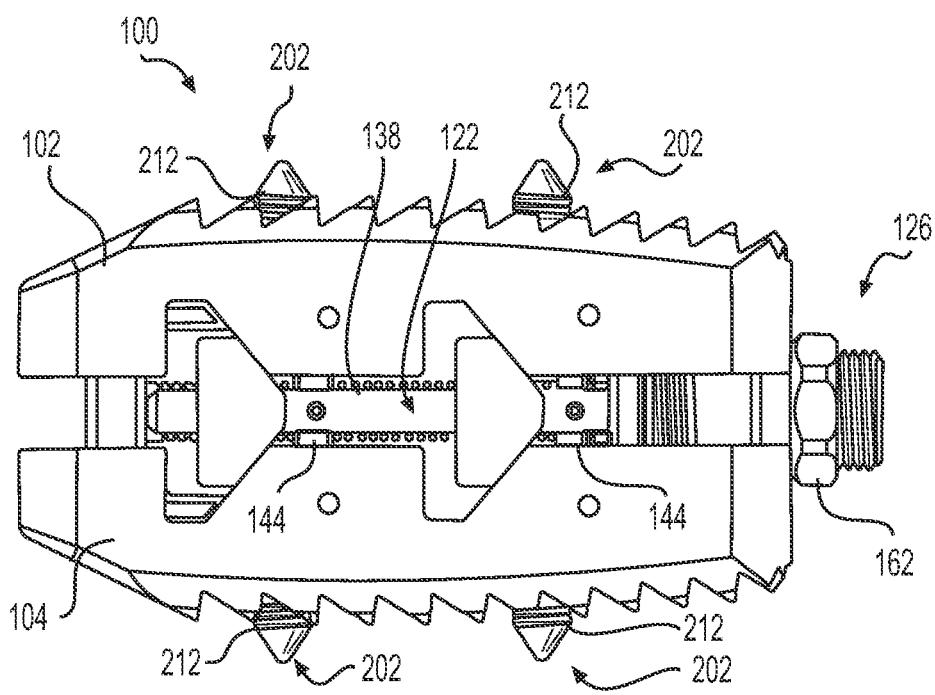
FIG. 30 is a side view of the spacer of FIG. 1 with body tissue engaging projections deployed.
Figure 31:
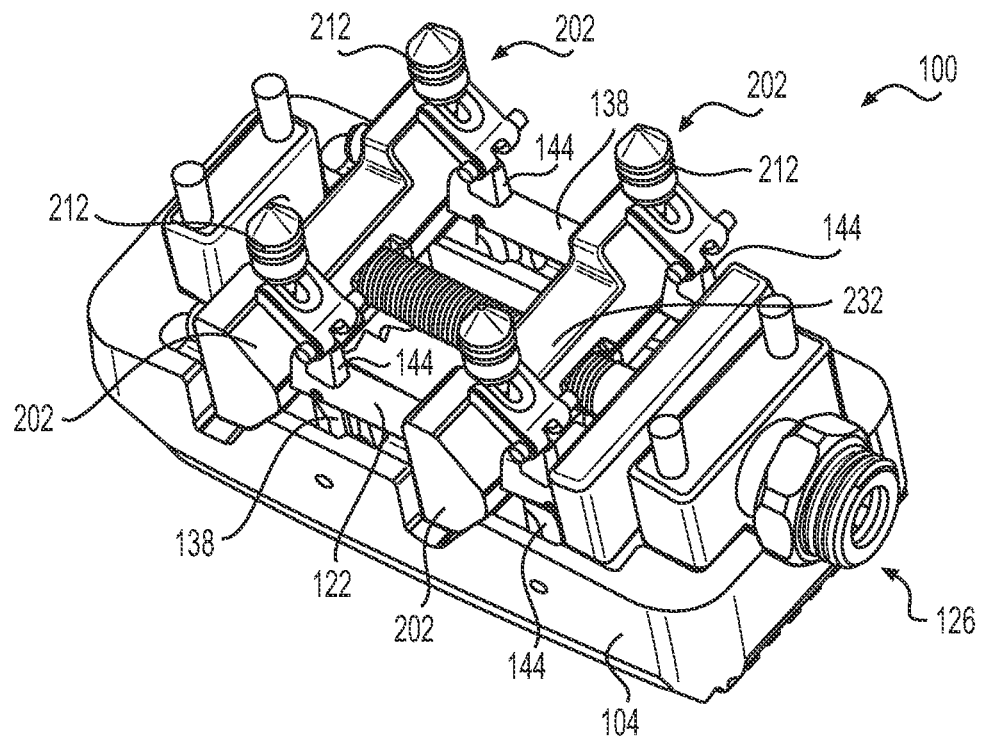
FIGS. 31 and 32 are cutaway views of the spacer of FIG. 1 with body tissue engaging projections deployed.
Figure 32:
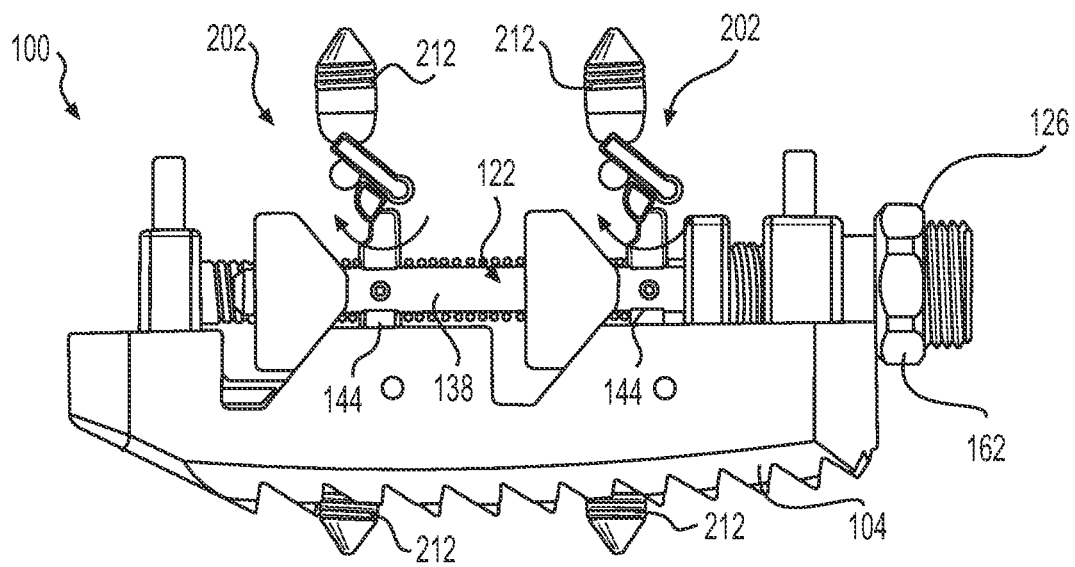

Referring now to FIGS. 1-3 and 23-32, operation of spacer 100 will now be described in accordance with example embodiments. FIGS. 1, 23, and 24 illustrate embodiments of spacer 100 in a collapsed configuration. FIGS. 2 and 25-28 illustrate embodiments of spacer 100 in an expanded configuration with tissue engaging projection subassemblies 202 retracted. FIGS. 3 and 29-32 illustrate embodiments of spacer 100 in an expanded configuration with tissue engaging projection subassemblies 202 deployed.

In operation, spacer 100 may be inserted between vertebral bodies when in a collapsed or non-expanded state, as illustrated on FIGS. 1, 23, and 24. In some embodiments, spacer 100 may be inserted from a lateral approach to the spine. In some embodiments, an insertion tool (not shown) may threadably engage threaded portion 153 of drive nut 126 and thus engage spacer 100 so that spacer 100 can be retained during insertion. After insertion, in some embodiments, a tool (not shown) may engage tool engagement portion 160 (best seen on FIG. 8) of drive shaft 128. While tool engagement portion 160 is obstructed from view on FIGS. 1, 23, and 24, in some embodiments, tool engagement portion 160 may be accessed via through bore 166 of drive nut 126. With additional reference to FIGS. 2 and 25-28, the tool may be used to rotate drive shaft 128 such that ramped carriages 108 may be withdrawn or advanced to cause expansion ramps 106 to slide along ramped carriages 108, thereby moving endplates 102, 104 such that a height of spacer 100 may be increased. In this manner, spacer 100 may be moved from a collapsed configuration (e.g., shown in FIGS. 1, 23, and 24) to an expanded configuration (e.g., shown in FIGS. 2 and 25-28). In some embodiments, the tissue engaging projection subassemblies 202 may be retracted during insertion and expansion of spacer 100. With additional reference to FIGS. 3 and 29-32, deployment of tissue engaging subassemblies 202 will now be described. In some embodiments, a tool (not shown) may be engaged with head portion 162 of drive nut 126. The tool may be used to rotate drive nut 126 causing advancement or retraction of projection actuation bar 122. As projection actuation bar 122 is advanced or retracted, plates 144 (e.g., coupled to arms 138 of projection actuation bar 122) should engage tissue engaging subassemblies 202 to cause projection members 212 to extend through endplates 102, 104. Because movement of tissue engaging subassemblies 202 is restrained in compartments 204 (e.g., shown on FIGS. 16 and 17), tissue engaging subassemblies 202 should pivot outward from spacer 100 when engaged by plates 144. In this manner, tissue engaging subassemblies 202 may be deployed after insertion and expansion of spacer 100, in accordance with example embodiments.

In some embodiments, spacer 100 may enable a continuous expansion and retraction over a range of displacements according to predetermined dimensions of a specific spacer design. This provides the ability to distract vertebral bodies or other bones to a desired height or separation. Endplates 102, 104 can be shaped to form planes or surfaces which converge relative to each, to provide for proper lordosis, and can be provided with through openings 192 (e.g., shown on FIGS. 13 and 14) through which bone may grow, and into which bone graft material may be placed. In some embodiments, spacer 100 may be used to distract, or force bones of a joint apart, or may be used to maintain a separation of bones created by other means, for example by a retractor. Endplates 102, 104 may additionally be curved to conform to the surface of body tissue, for example the surface of cortical bone, of the vertebra to be contacted, for improved fixation and load bearing.

In some embodiments, spacer 100 may be fabricated using any biocompatible materials known or hereinafter discovered, having sufficient strength, flexibility, resiliency, and durability for the patient, and for the term during which the device is to be implanted. Examples include but are not limited to metal, such as, for example titanium and chromium alloys; stainless steel, polymers, including for example, PEEK or high molecular weight polyethylene (HMWPE); and ceramics. There are many other biocompatible materials which may be used, including other plastics and metals, as well as fabrication using living or preserved tissue, including autograft, allograft, and xenograft material. Portions or all of the spacer 100 may be radiopaque or radiolucent, or materials having such properties may be added or incorporated into the spacer 100 to improve imaging of the device during and after implantation. Any surface or component of a spacer 100 may be coated with or impregnated with therapeutic agents, including bone growth, healing, antimicrobial, or drug materials, which may be released at a therapeutic rate, using methods known to those skilled in the art.

In some embodiments, spacer 100 may be formed using titanium, or a cobalt-chrome-molybdenum alloy, Co—Cr—Mo, for example as specified in ASTM F1537 (and ISO 5832-12). The smooth surfaces may be plasma sprayed with commercially pure titanium, as specified in ASTM F1580, F1978, F1147 and C-633 (and ISO 5832-2). Alternatively, part or all of spacers 100 may be formed with a polymer, for example ultra-high molecular weight polyethylene, UHMWPE, for example as specified in ASTM F648 (and ISO 5834-2). In one embodiment, PEEK-OPTIMA (a trademark of Invibio Ltd Corp, United Kingdom) may be used for one or more components of the disclosed spacers 100. For example, polymeric portions can be formed with PEEK-OPTIMA, which is radiolucent, whereby bony ingrowth may be observed. Other polymeric materials with suitable flexibility, durability, and biocompatibility may also be used.

In accordance with present embodiments, spacer 100 may be provided in various sizes to best fit the anatomy of the patient. Components of matching or divergent sizes may be assembled during the implantation procedure by a medical practitioner as best meets the therapeutic needs of the patient, the assembly inserted within the body using an insertion tool. In some embodiments, spacer 100 may also be provided with an overall angular geometry, for example an angular mating disposition of endplates, to provide for a natural lordosis, or a corrective lordosis, for example of from 0° to 12° for a cervical application, although much different values may be advantageous for other joints. Lordotic angles may also be formed by shaping one or both endplates to have relatively non-coplanar surfaces.

In some embodiments, expanded height of spacer 100 for use in the cervical vertebrae, for example, may typically range from 7 mm to 12 mm, but may be larger or smaller, including as small as 5 mm, and as large as 16 mm, although the size is dependent on the patient, and the joint into which spacer 100 may be implanted. A spacer 100 may be implanted within any level of the spine, and may also be implanted in other joints of the body, including joints of the hand, wrist, elbow, shoulder, hip, knee, ankle, or foot.

In some embodiments, a single spacer 100 may be used, to provide stabilization for a weakened joint or joint portion. Alternatively, a combination of two, three, or more of any of spacer 100 may be used, at a single joint level, or in multiple joints. Moreover, implants of the disclosure may be combined with other stabilizing means.

In some embodiments, a spacer 100 may be fabricated using material that biodegrades in the body during a therapeutically advantageous time interval, for example after sufficient bone ingrowth has taken place. Further, implants of the disclosure are advantageously provided with smooth and or rounded exterior surfaces, which reduce a potential for deleterious mechanical effects on neighboring tissues.

In some embodiments, a spacer 100 may be provided to be support adjacent vertebrae during flexion/extension, lateral bending, and axial rotation. In one embodiment, spacer 100 is indicated for spinal arthroplasty in treating skeletally mature patients with degenerative disc disease, primary or recurrent disc herniation, spinal stenosis, or spondylosis in the lumbosacral spine (LI-SI). The surgery to implant spacer 100 may be performed through an Anterior, Anterolateral, Posterolateral, Lateral, or any other approach.

The terms "a" or "an", as used herein, are defined as one or more than one. The term plurality, as used herein, is defined as two or more than two. The term another, as used herein, is defined as at least a second or more. The terms "including" and "having," as used herein, are defined as comprising (i.e., open language).

Although the present invention and its advantages have been described in detail, it should be understood that various changes, substitutions and alterations may be made herein without departing from the spirit and scope of the invention as defined by the appended claims

What is claimed is:

1. A spacer for separating bones of a joint, the spacer comprising:
   a first endplate configured to engage a first bone of the joint, and including a ramped surface;
   at least one spike adapted to project out of the first endplate and pierce the first bone in engagement with the first endplate;
   a second endplate configured to engage a second bone of the joint; and
   a frame subassembly disposed between the first endplate and the second endplate,
   wherein the frame subassembly comprises:
      a drive shaft;
      a ramped carriage coupled to the drive shaft and including a ramped surface operable to engage the ramped surface of the first endplate, the drive shaft operable to drive the ramped carriage to move the first endplate relative to the second endplate;
      a drive nut disposed coaxially over and around the drive shaft, and adapted to rotate independently of the drive shaft;
      an actuation bar adapted to slide upon rotation of the drive nut so as to extend the spike through the first endplate.

2. The spacer of claim 1, wherein the spike is disposed in a compartment of the first endplate.

3. The spacer of claim 2, wherein the spike is part of a spike assembly and the spike assembly is pivotally coupled to the first endplate.

4. The spacer of claim 1, wherein the spacer is moveable from a collapsed position to an expanded position from rotation of the drive shaft, wherein in the expanded position the spacer has a height that is greater than a height in the collapsed position.

5. The spacer of claim 1, wherein the spike includes a tissue engaging end in the form of a conical spike.

6. The spacer of claim 1, further comprising a base coupled to the spike and including a downward projection that engages the actuation bar.

7. The spacer of claim 1, further comprising a base pivotally coupled to the first endplate, wherein the spike is coupled to the base and rotation of the base by the actuation bar causes the spike to project out of the first endplate.

8. The spacer of claim 7, further comprising a cam bar attached to the actuation bar and adapted to engage the base.

9. The spacer of claim 1, wherein the spike is part of a spike assembly and the spike assembly is pivotally coupled to the first endplate and rotation of the spike assembly causes the spike to project out of the first endplate.

10. The spacer of claim 1, wherein the ramped carriage is threadingly engaged with the drive shaft.

11. The spacer of claim 1, wherein the drive nut includes a head and an extension from the head, the extension having a threaded portion, wherein the actuation bar is threadingly engaged with the threaded portion of the extension.

12. The spacer of claim 11, wherein the actuation bar includes a base plate having a through bore through which the extension of the drive nut extends, and a pair of arms that extend from the base plate toward a distal end of the spacer.

13. The spacer of claim 12, wherein the arms of the actuation bar extend through the ramped carriage.

14. The spacer of claim 12, further comprising a plate operable to engage the spike and disposed in a slot in one of the arms of the actuation bar.

15. A spacer for separating bones of a joint, the spacer comprising:
- a first endplate configured to engage a first bone of the joint, and including a ramped surface;
- at least one spike adapted to project out of the first endplate and pierce the first bone in engagement with the first endplate;
- a second endplate configured to engage a second bone of the joint; and
- a frame subassembly disposed between the first and second endplates;
- wherein the frame subassembly comprises:
  - a drive shaft having an external threading;
  - a ramped carriage threadingly coupled to the drive shaft and including a ramped surface operable to engage the ramped surface of the first endplate, rotation of the drive shaft driving the ramped carriage to move the first endplate relative to the second endplate;
  - a drive nut disposed coaxially over and around the drive shaft, and adapted to be rotatable independently of the drive shaft;
  - an actuation bar threadingly coupled to an external threading of the drive nut and adapted to slide upon rotation of the drive nut so as to extend the spike through the first endplate.

16. The spacer of claim 15, wherein the at least one spike includes first and second spikes, the actuation bar including:
- a base plate threadingly coupled to the external threading of the drive nut;
- a pair of opposing arms that extend from the base plate toward a distal end of the spacer, the opposing arms extending through the ramped carriages; and
- plates disposed in spaced slots formed in each of the opposing arms of the actuation bar, wherein the plates are operable to engage the first and second spikes.

17. The spacer of claim 15, further comprising a base coupled to the spike and including a downward projection that engages the actuation bar.

18. The spacer of claim 15, further comprising a base pivotally coupled to the first endplate, wherein the spike is coupled to the base and rotation of the base by the actuation bar causes the spike to project out of the first endplate.

19. The spacer of claim 18, further comprising a cam bar attached to the actuation bar and adapted to engage the base.

20. The spacer of claim 15, wherein the spike is part of a spike assembly and the spike assembly is pivotally coupled to the first endplate.

* * * * *